(12) United States Patent
Terbrueggen

(10) Patent No.: US 10,829,803 B2
(45) Date of Patent: *Nov. 10, 2020

(54) DETECTION OF NUCLEIC ACID TARGETS USING CHEMICALLY REACTIVE OLIGONUCLEOTIDE PROBES

(75) Inventor: Robert Terbrueggen, Manhattan Beach, CA (US)

(73) Assignee: DXTERITY DIAGNOSTICS INCORPORATED, Rancho Dominguez, CA (US)

( * ) Notice: Subject to any disclaimer, the term of this patent is extended or adjusted under 35 U.S.C. 154(b) by 242 days.

This patent is subject to a terminal disclaimer.

(21) Appl. No.: 11/801,990

(22) Filed: May 10, 2007

(65) Prior Publication Data
US 2008/0124810 A1 May 29, 2008

Related U.S. Application Data

(60) Provisional application No. 60/746,897, filed on May 10, 2006.

(51) Int. Cl.
| C12Q 1/68 | (2018.01) |
| C12Q 1/6827 | (2018.01) |
| C12Q 1/6858 | (2018.01) |
| C12Q 1/6818 | (2018.01) |
| C07H 21/04 | (2006.01) |

(52) U.S. Cl.
CPC ......... *C12Q 1/6827* (2013.01); *C12Q 1/6818* (2013.01); *C12Q 1/6858* (2013.01); *Y10T 436/143333* (2015.01)

(58) Field of Classification Search
None
See application file for complete search history.

(56) References Cited

U.S. PATENT DOCUMENTS

| 4,469,863 A | 9/1984 | Ts'o et al. |
| 5,034,506 A | 7/1991 | Summerton et al. |
| 5,185,243 A | 2/1993 | Ullman et al. |
| 5,216,141 A | 6/1993 | Benner |
| 5,235,033 A | 8/1993 | Summerton et al. |
| 5,346,994 A | 9/1994 | Chomczynski |
| 5,386,023 A | 1/1995 | Sanghvi et al. |
| 5,476,930 A | 12/1995 | Letsinger et al. |
| 5,514,546 A | 5/1996 | Kool |
| 5,602,240 A | 2/1997 | De Mesmaeker |
| 5,637,684 A | 6/1997 | Cook et al. |
| 5,644,048 A | 7/1997 | Yau |
| 5,674,683 A | 10/1997 | Kool |
| 5,681,943 A * | 10/1997 | Letsinger et al. ......... 536/25.33 |
| 5,683,874 A | 11/1997 | Kool |
| 5,714,320 A | 2/1998 | Kool |
| 5,780,613 A | 7/1998 | Letsinger et al. |
| 5,808,036 A | 9/1998 | Kool |
| 5,876,924 A | 3/1999 | Zhang et al. |
| 6,077,668 A | 6/2000 | Kool |
| 6,140,480 A | 10/2000 | Kool |
| 6,218,108 B1 | 4/2001 | Kool |
| 6,265,166 B1 | 7/2001 | Frank-Kamenetskii et al. |
| 6,479,650 B1 | 11/2002 | Kool |
| 6,511,810 B2 | 1/2003 | Bi et al. |
| 6,670,193 B2 | 12/2003 | Kool |
| 6,942,771 B1 | 9/2005 | Kayyem |
| 6,955,901 B2 | 10/2005 | Schouten |
| 7,033,753 B1 | 4/2006 | Kool |
| 7,153,658 B2 | 12/2006 | Anderson et al. |
| 7,198,900 B2 | 4/2007 | Woudenberg et al. |
| 2002/0197630 A1 | 12/2002 | Knapp et al. |
| 2004/0110134 A1 | 6/2004 | Wenz et al. |
| 2004/0214196 A1 | 10/2004 | Aydin |
| 2004/0235005 A1 | 11/2004 | Friedlander et al. |
| 2004/0235154 A1 | 11/2004 | Oh et al. |
| 2004/0259102 A1 * | 12/2004 | Kool .................... C12Q 1/6818 435/6.11 |
| 2004/0259105 A1 | 12/2004 | Fan et al. |
| 2005/0142545 A1 * | 6/2005 | Conn et al. ...................... 435/6 |
| 2005/0142577 A1 | 6/2005 | Jones et al. |

(Continued)

FOREIGN PATENT DOCUMENTS

| EP | 320308 | 6/1989 |
| EP | 439182 | 7/1991 |

(Continued)

OTHER PUBLICATIONS

"How many species of bacteria are there" (wisegeek.com; accessed Sep. 23, 2011).*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"List of sequenced bacterial genomes" (Wikipedia.com; accessed Jan. 24, 2014).*
Abe and Kool, "Destabilizing Universal Linkers for Signal Amplification in Self-Ligating Probes for RNA," Journal of the American Chemical Society, 2004, 126(43), 13980-13986.*
"List of Sequenced Animal Genomes," Wikipedia.com, Jan. 19, 2018, 29 pages.*

(Continued)

*Primary Examiner* — Bradley L. Sisson
(74) *Attorney, Agent, or Firm* — Morgan, Lewis & Bockius LLP; Robin M. Silva; Louis T. Nguyen

(57) ABSTRACT

The present invention provides compositions, apparatuses and methods for detecting one or more nucleic acid targets present in a sample. Methods of the invention include utilizing two or more oligonucleotide probes that reversibly bind a target nucleic acid in close proximity to each other and possess complementary reactive ligation moieties. When such probes have bound to the target in the proper orientation, they are able to undergo a spontaneous chemical ligation reaction that yields a ligated oligonucleotide product. In accordance with the invention, the presence of the target(s) of interest can be determined by measuring the presence or amount of ligated oligonucleotide product.

10 Claims, 16 Drawing Sheets

Specification includes a Sequence Listing.

(56) References Cited

U.S. PATENT DOCUMENTS

| | | | |
|---|---|---|---|
| 2005/0208503 | A1 | 9/2005 | Yowanto et al. |
| 2005/0208543 | A1 | 9/2005 | Vann et al. |
| 2005/0272071 | A1 | 12/2005 | Lao et al. |
| 2006/0003351 | A1 | 1/2006 | Karger et al. |
| 2006/0063163 | A1 | 3/2006 | Chen et al. |
| 2006/0068378 | A1 | 3/2006 | Mirkin et al. |
| 2006/0094021 | A1* | 5/2006 | Costa ............ A61K 31/28 435/6.14 |
| 2006/0199192 | A1 | 9/2006 | Kool et al. |
| 2007/0072821 | A1 | 3/2007 | Iakoubova et al. |
| 2008/0124810 | A1 | 5/2008 | Terbrueggen |
| 2008/0242560 | A1 | 10/2008 | Gunderson et al. |
| 2010/0267585 | A1 | 10/2010 | Terbrueggen |
| 2013/0005594 | A1* | 1/2013 | Terbrueggen et al. ....... 506/9 |

FOREIGN PATENT DOCUMENTS

| | | |
|---|---|---|
| EP | 1130113 A1 | 9/2001 |
| WO | WO/1989/12696 | 12/1989 |
| WO | WO 1990/001069 | 2/1990 |
| WO | WO 1992/003576 | 8/1991 |
| WO | WO 1992/020702 | 11/1992 |
| WO | WO 1994/024143 A1 | 10/1994 |
| WO | WO/1994/29485 | 12/1994 |
| WO | WO 1995/015971 | 6/1995 |
| WO | WO 1996/015271 | 11/1995 |
| WO | WO/1996/35699 | 11/1996 |
| WO | WO 1996/040712 | 12/1996 |
| WO | WO 1997/031256 | 8/1997 |
| WO | WO 1997/046568 | 12/1997 |
| WO | WO 1998/020162 | 5/1998 |
| WO | WO 1999/037819 | 7/1999 |
| WO | WO/2001/27326 | 4/2001 |
| WO | WO 2001/092579 A2 | 12/2001 |
| WO | WO 2001/094638 | 12/2001 |
| WO | WO 2002/002823 | 1/2002 |
| WO | WO 2004/005545 A1 | 1/2004 |
| WO | WO/2004/076692 | 9/2004 |
| WO | WO 2007/133703 | 11/2007 |
| WO | WO 2010/114599 | 10/2010 |

OTHER PUBLICATIONS

Ueno, Y. et al., "Nucleosides and Nucleotides. 165. Chemical Ligation of Oligodeoxynuclotides Having a Mercapto Group at the 5-Position of 2'-Deoxyuridine Via a Disulfide Bond" *Nucleosides and Nucleotides*, Marcel Dekker Inc., vol. 17, No. 1-3 (1998) pp. 283-289.
Abe et al., "Destabilizing Universal Linkers for Signal Amplification in Self-Lighting Probes for RNA" *J. Am. Chem. Soc.* (2004) 126:13980:13986.
Abe et al., "Flow cytometric detection of specific RNAS in native human cells with quenched autoligating FRET probes" *Proc. Natl. Acad. Sci. USA* (2006) 103(2):263-8.
Abramson et al., "Nucleic acid amplification technologies" *Current Opinion in Biotechnology* (1993) 4:41-47.
Arar et al., "Synthesis and Antiviral Activity of Peptide-Oligonucleotide Conjugates Prepared by Using $N_\alpha$ (Bromoacetyl) peptides" *BioConj. Chem.* (1995) 6:573.
Bachmann et al., "Improvement of PCR amplified DNA sequencing with the aid of detergents" *Nucleic Acid Res.* (1990) 18:1309.
Backes et al., "An Alkanesulfonamide 'Safety-Catch' Linker for Solid-Phase Synthesis" *J. Org. Chem.* 64:2322-2330.
Baselt, D.R. et al., "A Biosensor Based on Magnetoresistance Technology", *Biosensors & Bioelectronics*, (1998) 13:731-739.
Beaucage et al., "The Functionalization of Oligonucleotides Via Phosphoramidite Derivatives" *Tetrahedron* (1993) 49(10):1925.
Bibikova, M. et al., "Quantitative Gene Expression Profiling in Formalin-Fixed, Paraffin-Embedded Tissues Using Universal Bead Arrays", *American Journal of Pathology*, (2004) 165:5 1799-1807.
Botti et al., "Chemical Synthesis of Proteins and Circular Peptides Using $N^\alpha$-1(1-Phenyl-2-Mercaptoethyl) Auxiliaries" *Protein Pept. Lett.* (2005) 12(8):729-35.
Brill et al., "Synthesis of Oligodeoxynucleoside Phosphorodithioates via Thioamidites" *J. Am. Chem. Soc.* (1989) 111:2321.
Carlsson et al., "Screening for genetic mutations" *Nature* (1996) 380:207.
Chan et al., "Construction and Characterization of a Heterodimeric Iron Protein: Defining Roles for Adenosine Triphosphate in Nitrogenase Catalysis" *Biochemistry* (2000) 39(24):7221-8.
Cuppolletti et al., "Oligomeric Fluorescent Labels for DNA" *Bioconjug. Chem.* (2005) 16(3):528-34.
Dempcy et al., "Synthesis of a thymidyl pentamer of deoxyribonucleic guanidine and binding studies with DNA homopolynucleotides" *Proc. Natl. Acad. Sci. USA* (1995) 92:6097.
Dill, K. et al., "Immunoassays and Sequence-Specific DNA Detection on a Microchip Using Enzyme Amplified Electrochemical Detection", *J. Biochem. Biophys. Methods*, (2004) 59:181-187.
Dogan et al., "5'-Tethered Stilbene Derivatives as Fidelity-and Affinity-Enhancing Modulators of DNA Duplex Stability" *J. Am. Chem. Soc.* (2004) 126:4762-4763.
Dose et al., "Convergent Synthesis of Peptide Nucleic Acids by Native Chemical Ligation", *Org. Letters* (2005) 7:20 4365-4368.
Dose et al., "Reducing Product Inhibition in DNA-Template-Controlled Ligation Reactions", *Agnew. Chem. Int. Ed.* (2006) 45:5369-5373.
Egholm, M. et al., "Peptide Nucleic Acids (PNA). Oligonucleotide Analogues with an Achiral Peptide Backbone" *J. Am. Chem. Soc.* (1992) 114:1895.
Egholm, M. et al. "PNA Hybridizes to Complementary Oligonucleotides Obeying the Watson-Crick Hydrogen-Bonding Rules", *Nature*, (1993) 365:566-568.
Fan, JB et al., "A Versatile Assay for High-Throughput Gene Expression Profiling on Universal Array Matrices", *Genome Research*, (2004) 14, 878-885.
Ficht et al., "Single-Nucleotide-Specific PNA-Peptide Ligation on Synthetic and PCR DNA Templates", *J. Am. Chem. Soc.* (2004)126:9970-9981.
Ficht et al. "As Fast and Selective as Enzymatic Ligations: Unpaired Nucleobases Increase the Selectivity of DNA-Controlled Native Chemical PNA Ligation" *ChemBioChem* (2005) 6:2098-2103.
Foss, R.D. et al., "Effects of Fixative and Fixation Time on the Extraction and Polymerase Chain Reaction Amplification of RNA from Paraffin-Embedded Tissue. Comparison of Two Housekeeping Gene mRNA Controls", *Diagn. Mol. Pathol.*, 3(3):148-155 (1994).
Gottesfeld, J.M. et al., "Sequence-specific Recognition of DNA in the Nucleosome by Pyrrole-Imidazole Polyamides" *J. Mol. Biol.* (2001) 309:615-629.
Grossman et al., "DNA-Catalyzed Transfer of a Reporter Group" *J. Am. Chem. Soc.* (2006) 128:15596-15597.
Gryaznov, S.M. and Letsinger, R.L., "Template controlled coupling and recombination of oligonucleotide blocks containing thiophosphoryl groups" *Nucleic Acids Research* (1993) 21:1403.
Gryaznov et al., "Chemical Ligation of Oligonucleotides in the Presence and Absence of Template", *J. Am. Chem. Soc.*, (1993) 115(9):3808-3809.
Gryaznov et al., "Enhancement of Selectivity in Recognition of Nucleic Acids via Chemical Autoligation", *Nucleic Acids Res.*, (1994) 22:2366-2369.
Herrlein and Letsinger, "A Covalent Lock for Self-Assembled Oligonucleotide Conjugates", *J. Am. Chem. Soc.*, (1995) 117:10151-10152.
Horn et al., "Oligonucleotides with Alternating Anionic and Cationic Phosphoramidate Linkages: Synthesis and Hybridization of Sterio-uniform Isomers", *Tetrahedron Letters* (1996) 37:743.
Jeffs et al., "Unusual conformation of a 3'-thioformacetal linkage in a DNA duplex" *J. Biomolecular NMR* (1994) 34:17.
Jenkins et al., "The Biosynthesis of Carbocyclic Nucleosides" *Chem. Soc. Rev.* (1995) pp. 169-176.
Kenner, G.W., "The Safety Catch Principle in Solid Phase Peptide Synthesis", *J. Chem. Soc.* (1971) pp. 636-637.
Kiedrowski et al., "Parabolic Growth of a Self-Replicating Hexadeoxynucleotide Bearing a 3'5'-Phosphoamidate Linkage" *Agnew. Chem. Intl. Ed.* English (1991) 30:423.

(56) References Cited

OTHER PUBLICATIONS

Kool, E.T. et al., "Convergent DNA synthesis: a non-enzymatic dimerization approach to circular oligodeoxynucleotides" *Nucleic Acid Res.* (1995) 23 (17):3547.
Koshkin et al., "LNA (Locked Nucleic Acid): An RNA Mimic Forming Exceeingly Stable LNA:LNA Duplexes" *J. Am. Chem. Soc.* (1998) 120:13252-3.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" *Tetrahedron* (1998) 54:3607-3630.
Kutyavin et al., "Oligonucleotides with conjugated dihydropyrroloindole tripeptides: base composition and backbone effects on hybridization" *Nucleic Acids Research* (1997) vol. 25, No. 18:3718-3723.
Kutyavin et al., "3'-Minor groove binder-DNA probes increase sequence specificity at PCR extension temeratures" *Nucleic Acids Research* (2000) vol. 28, No. 2:655-661.
Landegren, U. "Ligation-based DNA Diagnostics" *Bioessays* (1993) 15(11):761-5.
Landegren, U. et al., "A Ligase-Mediated Gene Detection Technique", *Science*, (1988) 241(4689):1077-1080.
Letsinger et al., "Phosphoramidate Analogs of Oligonucleotides" *J. Org. Chem.* (1970) 35:3800.
Letsinger et al., *Nucl. Acids Res.* (1986) 14:3487.
Letsinger et al., "Cationic Oligonucleotides" *J. Am. Chem. Soc.* (1988) 110:4470.
Letsinger et al., "Hybridization of Alternating Cationic/Anionic Oligonucleotides to RNA Segments", *Nucleotide and Nucleoside* (1994) 13:1597.
Liu, R. et al., "Fully Integrated Miniature Device for Automated Gene Expression DNA Microarray Processing", *Anal. Chem.*, (2006) 78(6):1980-1986.
Luebke and Dervan, "Nonenzymatic Sequence-Specific Ligation of Double-Helical DNA", *J. Am. Chem. Soc.*, (1991) 113:7447-7448.
Luebke, K.J. and Dervan, P.B., "Nonenzymatic Ligation of Oligodeoxyribonucleotides no a Duplex DNA Template by Triple-Helix Formation", *J. Am. Chem. Soc.* (1989) 111:8733.
Mag et al., "Synthesis and selective cleavage of an oligodeoxynucleotide containing a bridged internucleotide 5'-phosphorothioate linkage", *Nucleic Acids Res.* (1991) 19:1437-1441.
Marshall et al., "DNA Chips: An Array of Possibilities", *Nat Biotechnol.* (1998) 16(1):27-31.
Martel et al., (High Throughput Genomics) "Multiplex Screening Assay for mRNA Combining Nuclease Protection with Luminescent Array Detection," *Assay and Drug Development Technologies* 1:61-71 (2002).
Meier et al., "Peptide Nucleic Acids (PNAs)—Unusual Properties of Nonionic Oligonucleotide Analogues" *Chem. Int. Ed. Engl.* (1992) 31:1008.
Mesmaeker et al., "Comparison of Rigid and Flexible Backbones in Antisense Oligonucleotides", *Bioorganic & Medicinal Chem. Lett.* (1994) 4:395.
Metelev, V.G. et al., "Oligodeoxyribonucleotides With Internucleotidic or Terminal Phosphorothioate Groups: Different Pathways in the Reaction with Water-Soluble Carbodimide", *Nucleosides & Nucleotides* (1999) 18:2711.
Moran et al., "A thymidine triphospate shape analog lacking Watson-Crick pairing ability is replicated with high sequence selectivity", *Proc. Natl. Acad. Sci. USA* (1997) 94(20):10506-11.
Narayanan et al., "Clamping down on weak terminal base pairs: oligonucleotides with molecular caps as fidelity-enhancing elements at the 5'- and 3'-terminal residues", *Nucleic Acids Research* (2004) 32:2901-2911.
Nickerson, "Gene probe assays and their detection", *Current Opinion in Biotechnology* (1993) 4:48-51.
Nilsson, M. et al., "RNA-Templated DNA Litigation for Transcript Analysis", *Nucleic Acids Research*, 29:2 578-581 (2001).

Offer et al., "Extending Synthetic Access to Proteins with a Removable Acyl Transfer Auxiliary", *J. Am. Chem. Soc.* (2002) 124(17):4642-6.
Ollivier et al., "Fmoc Solid-Phase Synthesis of Peptide Thioesters Using an Intramolecular N,S-Acyl Shift" *Organic Letters* (2005) vol. 7, No. 13, pp. 2647-2650.
Pauwels et al., "Biological Activity of New 2-5A Analogues", *Chemica Scripta* (1986) 26:141.
Pooga, M. et al., "PNA oligomers as tools for specific modulation of gene expression", *Biomolecular Engineering* (2001) 17:183-192.
Pritchard et al., "Effects of Base Mismatches on Joining of Short Oligonucleotides by DNA Ligases", *Nucleic Acids Res.* (1997) 25(17):3403-7.
Rawls, R.,"Optimistic About Antisense "*C & E News* (Jun. 2, 1997), p. 35-39.
Sando et al., "Nonenzymatic DNA ligation in *Escherichia coli* cells", *Nucleic Acids Res. Suppl.* (2002) 2:121-2.
Sando et al., "Quencher as Leaving Group: Efficient Detection of DNA-Joining Reactions", *J. Am. Chem. Soc.* (2002) 124(10)2096-7.
Sando et al., "Imaging of RNA in Bacteria with Self-Ligating Quenched Probes", *Journal Am. Chem.* (2002) 124(33):9686-7.
Sando et al., "Quenched Auto-Ligating DNAs: Multicolor Identification of Nucleic Acids at Single Nucleotide Resolution", *J. Am. Chem. Soc.* (2004) 126(4):1081-7.
Sawai et al., "Synthesis and Properties of Oligoadenylic Acids Contaiing 2'-5' Phosphoramide Linkage", *Chem. Lett.* (1984) 805.
Schafer et al., "DNA variation and the future of human genetics", *Nature Biotechnology* (1993) 16:33-39.
Shabarova, Z.A., et al., "Chemical ligation of DNA: the first non-enzymatic assembly of a biologically active gene", *Nucleic Acids Research* (1991) 19:4247.
Shanghvi, Y.S. and Cook, Dan (Ed.) "ASC Symposium Series 580", Chapters 2, 3, 6, and 7.
Silverman et al., "Quenched autoligation probes allow discrimination of live bacterial species by single nucleotide differences in rRNA", *Nucleic Acids Res.* (2005) 33(15):4978-86.
Silverman et al., "Detecting RNA and DNA with Templated Chemical Reactions", *Chem. Rev.*, (2006) 106:3775-3789.
Sprinzl et al., "Enzymatic Incorporation of ATP and CTP Analogues into the 3' End of Trna", *Eur. J. Biochem.* (1977) 81:579.
Steemers, F.J. et al., "Screening Unlabeled DNA Targets with Randomly Ordered Fiber-Optic Gene Arrays", *Nat Biotechnol.* (2000) 18(1):91-4.
Stetsenko and Gait, "Efficient Conjugation of Peptides to Oligonucleotides by 'Native Ligation'", *J. Org. Chem.* (2000) 65(16):4900-8.
Umek, R.M. et al., "Electronic Detection of Nucleic Acids—A Versatile Platform for Molecular Diagnostics", *J. Molecular Diagnostics*, (2001) 3:74-84.
Van't Veer, L.J., et al., "Gene Expression Profiling Predicts Clinical Outcome of Breast Cancer", *Nature*, (2002) 415(6871):530-536 (2002).
Wahlestedt C. et al., "Potent and nontoxic antisense oligonucleotides containing locked nucleic acids", *PNAS* (2000) 97:5633-5638.
Wang et al., "Large-Scale Identification, Mapping, and Genotyping of Single-Nucleotide Polymorphisms in the Human Genome", *Science* (1998) 280:1077.
Warren et al., "Toward Fully Synthetic Glycoproteins by Ultimately Convergent Routs: A Solution to a Long-Standing Problem", *J. Am. Chem. Soc.* (2004) 126(21):6576-82.
Weizmann, Y. et al., "Magneto-Mechanical Detection of Nucleic Acids and Telomerase Activity in Cancer Cells", *J. Am. Chem. Soc.*, (2004) 126:1073-1080.
Wengel, J. et al., "LNA (Locked Nucleic Acid)", *Nucleosides & Nucleotides*, (1999) 18:1365-1370.
Wu, D.Y. et al., "The LIgation Amplification Reaction (LAR)—Amplification of Specific DNA Sequences Using Sequential Rounds of Template-Dependent Ligation", *Genomics* (1989) 4(4):560-9.
Xu et al., "Chemical and enzymatic properties of bridging 5'-S-phosphorothioester linkages in DNA", *Nucleic Acid Res.* (1998) 26(13):3159-64.

(56) References Cited

OTHER PUBLICATIONS

Xu et al., "Nonenzymatic Autoligation in Direct Three-Color Detection of RNA and DNA Point Mutations" *Nature Biotechnology* (2001) 19(2):148-52.

Xu and Kool, E.T., "A Novel 5'-Iodonucleoside Allows Efficient Nonenzymatic Ligation of Single-stranded and Duplex DNAs", *Tetrahedron Letters* (1997) 38:5595.

Xu and Kool, E.T., "High sequence fidelity in a non-enzymatic DNA autoligation reacation", *Nucleic Acid Research* (1999) 27:875.

Yang et al., "Badge, Beads Array for the Detection of Gene Expression, a High Throughput Diagnostic Bioassay", *Genome Research* (2001) 11(11):1888-98.

Yeakley, JM et al., "Profiling Alternative Splicing on Fiber-Optic Arrays", *Nature Biotechnology*, (2002) 20:353-358.

Miller, G.P. et al., "New, stronger nucleophiles for nucleic acid-templated chemistry: Synthesis and application in fluorescence detection of cellular RNA", Bioorganic and Medicinal Chemistry (2008) 16:56-64.

Grossman et al., "High-Density Multiplex Detection of Nucleic Acid Sequences: Oligonucleotide Ligation Assay and Sequence-Coded Separation", *Nucleic Acids Research*, Oxford University Press, Surrey, Great Britain, vol. 22, No. 21, pp. 4527-4534 (1994).

Karim et al., "Convenient genotyping of six myostatin mutation causeing double-muscling in cattle using a multiplex oligonucleotide ligation assay", *Animal Genetics*, vol. 31, No. 6, pp. 396-399 (2000).

Schouten et al., "Relative quantification of 40 nucleic acid sequences by multiplex ligation-dependent probe amplification", *Nucleic Acid Research*, Oxford University Press, Great Britain, vol. 30, No. 12 (2002).

Stern et al., "Multiplex ligation-dependent probe amplification using a completely synthetic probe set", *Biotechniques*, vol. 37, No. 3, pp. 399-405 (2004).

Van Eijk, M.J.T., "SNPWaveTM: a flexible multiplexed SNP genotyping technology", *Nucleic Acids Research*, vol. 32, No. 4 (2004).

Castiglioni et al., "Development of a Universal Microarray Based on the Ligation Detection Reaction and 16S rRNA Gene Polymorphism to Target Diversity of Cyanobacteria", *Applied and Environmental Microbiology*, vol. 70, No. 12, pp. 7161-7172 (2004).

Hsuih, T. et al., "Novel, Ligation-Dependent PCR Assay for Detection of Hepatitis C Virus in Serum," J. Clin. Microbiology, vol. 34, No. 3, p. 501-507 (1996).

Li Jinghuan et al BMC Biotechnology 7 (1) 36 (2007).

\* cited by examiner

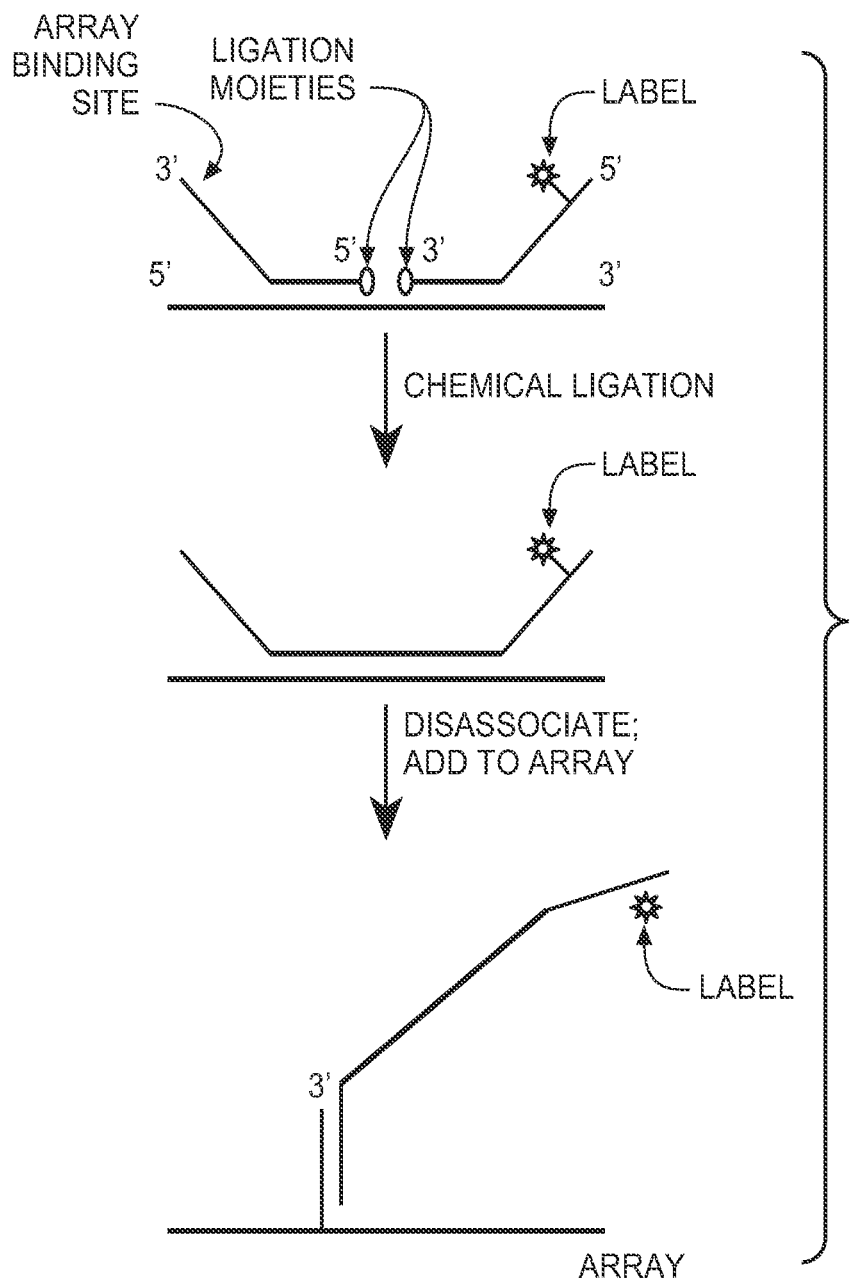
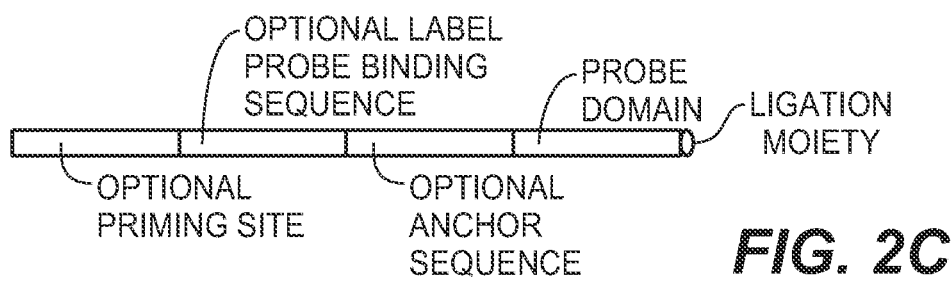
FIG. 2B
FIG. 2C

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial
<220> FEATURE:
<223> OTHER INFORMATION: Synthetic

<400> SEQUENCE: 1
gtaagtagac ataac                                                      15

<210> SEQ ID NO 2
<211> LENGTH: 23
<212> TYPE: DNA
<213> ORGANISM: Artificial
<220> FEATURE:
<223> OTHER INFORMATION: Synthetic

<400> SEQUENCE: 2
aaagacattc atctgtattg aaa                                             23

<210> SEQ ID NO 3
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Fluorescein dT phosphoramidite

<400> SEQUENCE: 3
acnccgacct tcacca                                                     16

<210> SEQ ID NO 4
<211> LENGTH: 14
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Fluorescein dT phosphoramidite

<400> SEQUENCE: 4
acngtggtca tgag                                                       14

<210> SEQ ID NO 5
<211> LENGTH: 12
<212> TYPE: DNA
<213> ORGANISM: Artificial
<220> FEATURE:
```

```
<223> OTHER INFORMATION: Synthetic

<400> SEQUENCE: 5
accaaatccg tt                                                          12

<210> SEQ ID NO 6
<211> LENGTH: 12
<212> TYPE: DNA
<213> ORGANISM: Artificial
<220> FEATURE:
<223> OTHER INFORMATION: Synthetic

<400> SEQUENCE: 6
agtgatggca tg                                                          12

<210> SEQ ID NO 7
<211> LENGTH: 29
<212> TYPE: DNA
<213> ORGANISM: Artificial
<220> FEATURE:
<223> OTHER INFORMATION: Synthetic

<400> SEQUENCE: 7
tgaaggtcgg agtaacggat ttggtcgta                                        29

<210> SEQ ID NO 8
<211> LENGTH: 28
<212> TYPE: DNA
<213> ORGANISM: Artificial
<220> FEATURE:
<223> OTHER INFORMATION: Synthetic

<400> SEQUENCE: 8
catgaccaca gtcatgccat cactgcca                                         28
```

DETECTION OF NUCLEIC ACID TARGETS USING CHEMICALLY REACTIVE OLIGONUCLEOTIDE PROBES

CROSS REFERENCE TO RELATED APPLICATIONS

This application claims priority to provisional application Ser. No. 60/746,897, filed on May 10, 2006, which is herein incorporated by reference in its entirety.

FIELD OF THE INVENTION

This invention relates to compositions and methods for detecting nucleic acids in a sample using chemical ligation.

BACKGROUND OF THE INVENTION

This invention relates to compositions, apparatus and methods for detecting one or more nucleic acid targets present in a sample. The detection of specific nucleic acids is an important tool for diagnostic medicine and molecular biology research.

Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology (1993) 4:48-51.) The requirement for sensitivity (i.e. low detection limits) has been greatly alleviated by the development of the polymerase chain reaction (PCR) and other amplification technologies which allow researchers to exponentially amplify a specific nucleic acid sequence before analysis (for a review, see Abramson et al., Current Opinion in Biotechnology, (1993) 4:41-47). For example, multiplex PCR amplification of SNP loci with subsequent hybridization to oligonucleotide arrays has been shown to be an accurate and reliable method of simultaneously genotyping hundreds of SNPs (see Wang et al., Science, (1998) 280:1077; see also Schafer et al., Nature Biotechnology, (1989)16:33-39). The drawback to such amplification technologies is their dependence on particular reagents, such as enzymes, which result in a need for subsequent purification procedures prior to detection.

Specificity also remains a problem in many currently available assays gene probe assays. The extent of molecular complementarity between probe and target defines the specificity of the interaction. Variations in probe composition, the concentrations of probes, of targets and of salts in the hybridization medium, in the reaction temperature, and in the length of the probe may alter or influence the specificity of the probe/target interaction.

It may be possible under some circumstances to distinguish targets with perfect complementarity from targets with mismatches, although this is generally very difficult using traditional technology, since small variations in the reaction conditions will alter the hybridization. New experimental techniques with the necessary specificity for mismatch detection with standard probes include probe digestion assays in which mismatches create sites for probe cleavage and DNA ligation assays where single point mismatches prevent ligation.

There are a variety of enzymatic and non-enzymatic methods available for detecting sequence variations. Examples of enzyme based methods to detect variations in nucleotide sequences include, but are not limited to, Invader™, oligonucleotide ligation assay (OLA) single base extension methods, allelic PCR, and competitive probe analysis (e.g. competitive sequencing by hybridization). Enzymatic DNA ligation reactions are well known in the genomics community (Landegren, Bioessays (1993) 15(11): 761-5; Pritchard et al., Nucleic Acids Res. (1997) 25(17): 3403-7; Wu et al., Genomics, (1989) 4(4):560-9). They have been used extensively in SNP detection, enzymatic amplification reactions and DNA repair.

A number of non-enzymatic or template mediated chemical ligation methods have been developed that can be used to detect sequence variations. These include chemical ligation methods that utilize coupling reagents, such as N-cyanoimidazole, cyanogen bromide, and 1-ethyl-3-(3-dimethylaminopropyl)-carbodiimide hydrochloride. See Metelev, V. G., et al., Nucleosides & Nucleotides (1999) 18:2711; Luebke, K. J., and Dervan, P. B. J. Am. Chem. Soc. (1989) 111:8733; and Shabarova, Z. A., et al., Nucleic Acids Research (1991)19:4247, each of which is incorporated herein by reference in its entirety.

Kool (U.S. Pat. No. 7,033,753), which is incorporated herein by reference in its entirety describes the use of chemical ligation and fluorescence resonance energy transfer (FRET) to detect genetic polymorphisms. The readout in this process is based on the solution phase change in fluorescent intensity.

Other chemical ligation methods react a 5'-tosylate or 5'-iodo group with a 3'-phosphorothioate group, resulting in a DNA structure with a sulfur replacing one of the bridging phosphodiester oxygen atoms. See Gryanov, S. M., and Letsinger, R. L., Nucleic Acids Research (1993) 21:1403; Xu, Y. and Kool, E. T. Tetrahedron Letters (1997) 38:5595; and Xu, Y. and Kool, E. T., Nucleic Acids Research (1999) 27:875, each of which is herein incorporated by reference in its entirety.

Some of the advantages of using non-enzymatic approaches for the nucleic acid target detection include lower sensitivity to non-natural DNA analog structures, ability to use RNA target sequences, lower cost and greater robustness under varied conditions. Letsinger et al (U.S. Pat. No. 5,780,613, herein incorporated by reference in its entirety) have previously described an irreversible, nonenzymatic, covalent autoligation of adjacent, template-bound oligonucleotides wherein one oligonucleotide has a 5' displaceable group and the other oligonucleotide has a 3' thiophosphoryl group.

PCT applications WO 95/15971, PCT/US96/09769, PCT/US97/09739, PCT US99/01705, WO96/40712 and WO98/20162, all of which are expressly incorporated herein by reference in their entirety, describe novel compositions comprising nucleic acids containing electron transfer moieties, including electrodes, which allow for novel detection methods of nucleic acid hybridization.

One technology that has gained increased prominence is DNA arrays (Marshall et al., Nat Biotechnol. (1998) 16(1): 27-31), especially for applications involving the simultaneous measurement of numerous nucleic acid targets. DNA arrays are most often used for gene expression monitoring where the relative concentration of 1 to 100,000 nucleic acids targets (mRNA) is measured simultaneously. DNA arrays are small devices in which nucleic acid anchor probes are attached to a surface in a pattern that is distinct and known at the time of manufacture (Marshall et al., Nat Biotechnol. (1998) 16(1):27-31) or can be accurately deciphered at a later time such as is the case for bead arrays (Steemers et al., *Nat Biotechnol.* (2000) 18(1):91-4; and Yang et al., *Genome Res.* (2001) 11(11):1888-98.). After a series of upstream processing steps, the sample of interest is brought into contact with the DNA array, the nucleic acid targets in the sample hybridize to anchor oligonucleotides on the surface, and the identity and often concentration of the target nucleic acids in the sample are determined.

Many of the nucleic acid detection methods in current use have characteristics and/or limitations that hinder their broad applicability or make them unsuitable for a given application. For example, in the case of DNA microarrays described above, prior to bringing the sample into contact with the microarray, there are usually a series of processing steps that must be performed on the sample so that they can be detected following hybridization to the DNA array. While these steps vary depending upon the manufacturer of the array and/or the technology that is used to read the array (fluorescence, electrochemistry, chemiluminescence, magnetoresistance, cantilever deflection, surface plasmon resonance), these processing steps usually fall into some general categories: Nucleic acid isolation and purification, enzymatic amplification, detectable label incorporation, and clean up post-amplification. Other common steps are sample concentration, amplified target fragmentation so as to reduce the average size of the nucleic acid target, and exonuclease digestion to convert PCR amplified targets to a single stranded species.

The need for so many upstream processing steps prior to contacting the DNA array with the sample can significantly increase the time and cost of detecting a nucleic acid target(s), and it can also have significant implications on the quality of the data obtained. For instance, some amplification procedures are very sensitive to target degradation and perform poorly if the input nucleic acid material is not well preserved (Foss et al., *Diagn Mol Pathol.* (1994) 3(3):148-55). New technologies that eliminate the need, reduce the complexity, and/or improve the performance of the upstream processing steps could significantly reduce the costs and improve the quality of results obtained from a DNA array based test.

One method for reducing upstream processing steps involves using ligation reactions to increase signal strength and improve specificity.

There remains a need for methods and compositions for efficient and specific nucleic acid detection. Accordingly, the present invention provides methods and compositions for non-enzymatic chemical ligation reactions which greatly simplify the process of detecting and measuring nucleic acid targets.

SUMMARY OF THE INVENTION

Accordingly, in one aspect, the invention comprises methods comprising providing a ligation substrate comprising a target sequence comprising at least a first target domain and a second target domain and a first and second ligation probe. The first ligation probe comprises a first probe domain substantially complementary to the first target domain and a 5'-ligation moiety. The second ligation probe comprises a second probe domain substantially complementary to the second target domain and a 3' ligation moiety. Optionally, at least one of the first and second target domains do not comprise PNA. Optionally, the first target domain and the second target domain are separated by at least one nucleotide. Optionally, at least one of the first and said second ligation probes comprises an anchor sequence and/or a label, including a label probe binding sequence. The first and second ligation probes are ligated in the absence of exogeneously added ligase enzyme to form a ligation product. The ligated product may optionally be capture on a substrate comprising a capture probe substantially complementary to said anchor sequence and detected.

d) detecting the presence of said ligated product.

BRIEF DESCRIPTION OF THE DRAWINGS

FIGS. 2A and 2B: FIG. 2A Schematic illustration of a chemical ligation probe set for nucleic acid detection, in which the upstream ligation probe contains an additional functional segment ("anchor probe") that does not bind the target nucleic acid but is present for subsequent binding to a capture probe of an array. The downstream probe possesses a label probe binding site that can be used for the binding of a universal fluorescent reporter. FIG. 2B depicts a similar reaction except the downstream probe comprises the label, and since capture is based on the upstream anchor probe, only ligated products will carry the label and be detected. The opposite orientation can also be done. In addition, as will be appreciated by those in the art, additional moieties can be included, as depicted in FIG. 2C, although the order is nondeterminative.

FIG. 11A is a specific reaction with specific linkages and FIG. 11B is a more generic version.

DETAILED DESCRIPTION OF THE INVENTION

Figure 1:
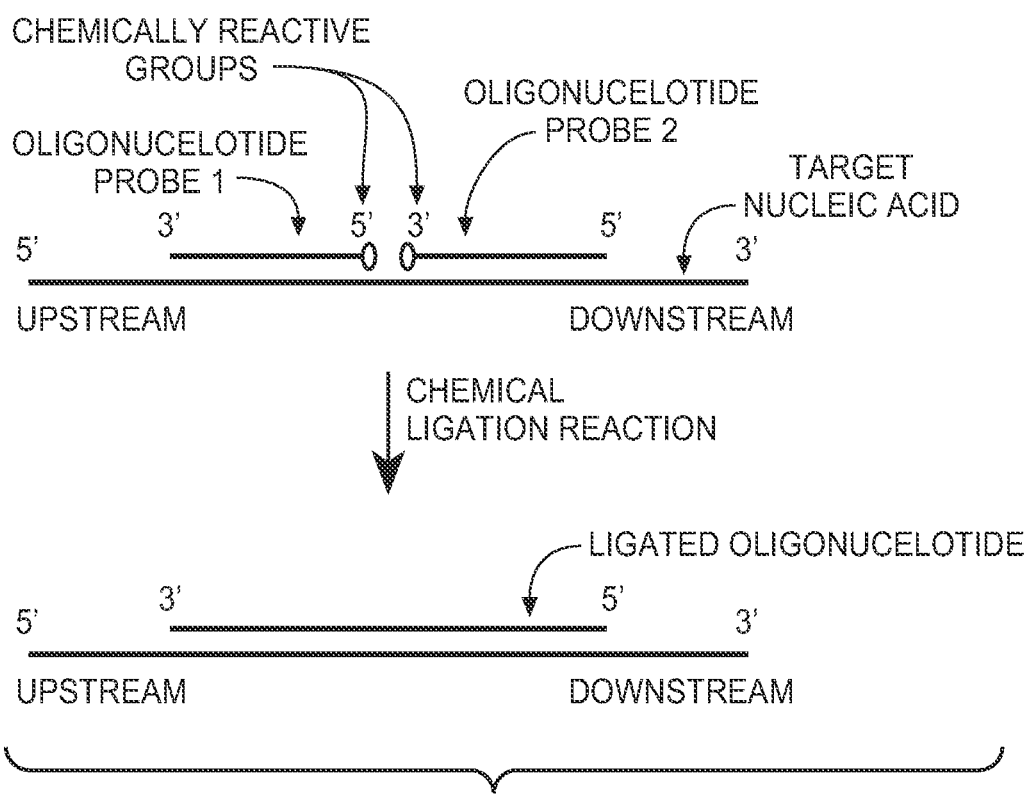
FIG. 1: Schematic illustration of a chemical ligation reaction, in which at least two oligonucleotide probes bind to a target nucleic acid in close proximity to each other. A chemically reactive group on the 5' end of the upstream oligonucleotide probe (Probe 1) reacts with a chemically reactive group on the 3' end of the downstream oligonucleotide probe (probe 2) and forms a ligated oligonucleotide.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) Biochemistry, $5^{th}$ Ed., W. H. Freeman Pub., New York, N.Y., all of which are hereby incorporated in their entirety by reference for all purposes. Furthermore, all references cited in this application are herein incorporated in their entirety by reference for all purposes.

Overview

The invention provides compositions, apparatus and methods for the detection of one or more nucleic acid targets in a sample. In general, this may be accomplished in several ways, including both a ligation reaction and a transfer reaction. The invention provides methods utilizing two or more oligonucleotide probes that reversibly bind a target nucleic acid in close proximity to each other and possess complementary reactive ligation moieties (it should be noted, as is further described herein, that the reactive moieties are referred to herein as "ligation moieties", even when a transfer reaction is occurring without ligation). In the ligation reaction, when the probes have bound to the target in the proper orientation, they are able to undergo a spontaneous chemical ligation reaction that yields a ligated oligonucleotide product. The presence of the target(s) of interest can then be determined by measuring the presence or amount of ligated oligonucleotide product. In accordance with the invention, the probes can possess detectable labels (fluorescent labels, electrochemical labels, magnetic beads, nanoparticles, biotin) to aid in the identification, quantification or detection of the ligated oligonucleotide product. The probes may also include in their structure: anchoring oligonucleotide sequences designed for subsequent capture on a solid support (microarrays, microbeads, nanoparticles), molecule handles that promote the concentration or manipulation of the ligated product (magnetic particles, oligonucleotide coding sequences), and promoter sequences to facilitate subsequent secondary amplification of the ligated product via an enzyme like a DNA or RNA polymerase. The ligation reactions of the invention proceed rapidly, are specific for the target(s) of interest, and can produce multiple copies of the ligated product for each target(s), resulting in an amplification (sometimes referred to herein as "product turnover") of the detectable signal. Preferably, the ligation reactions of the invention do not require the presence of exogeneously added ligases, nor additional enzymes, although some secondary reactions may rely on the use of enzymes such as polymerases, as described below. Amplification of the target may also include turnover of the ligation product, in which the ligation product has a lower or comparable affinity for the template or target nucleic acid than do the separate ligation probes. Thus, upon ligation of the hybridized probes, the ligation product is released from the target, freeing the target to serve as a template for a new ligation reaction.

In one embodiment, the ligation reactions of the invention include transfer reactions. In this embodiment, the probes hybridize to the target sequence, but rather than oligonucleotide probes being ligated together to form a ligation product, a nucleic acid-directed transfer of a molecular entity (including reporter molecules such as fluorophores, quenchers, etc) from one oligonucleotide probe to other occurs. This transfer reaction is analogous to a ligation reaction, however instead of joining of two or more probes, one of the probes is ligated to the transfer molecule and the other probe is the "leaving" of the chemical reaction. We use the term "transfer" reaction so as to distinguish between the different nature of the resulting final product. Importantly, similar to the ligation reaction, the transfer reaction is facilitated by the proximal binding of the transfer probes onto a nucleic acid target, such that significant signal is detected only if the probes have hybridized to the target nucleic acid in close enough proximity to one another (e.g., at adjacent sites) for the transfer reaction to take place.

Figure 14A:
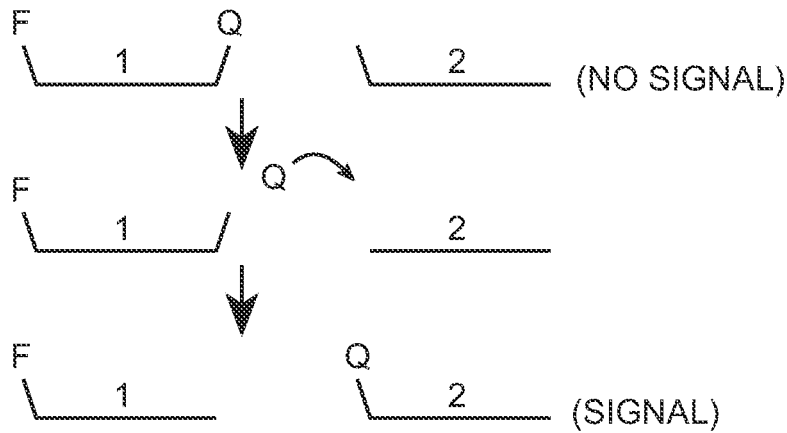
FIG. 14 is a schematic representation of transfer ligation reactions in which a reporter molecule is transferred from one ligation probe to another ligation probe hybridized to the target nucleic acid in an adjacent/nearby position.
Figure 14B:
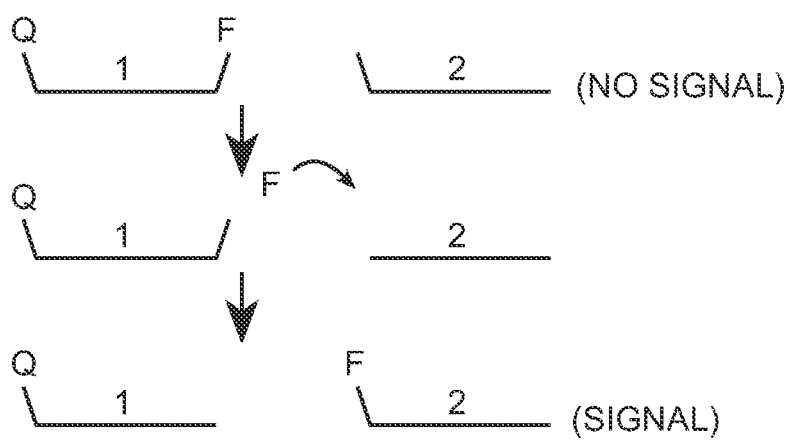
Figure 14C:
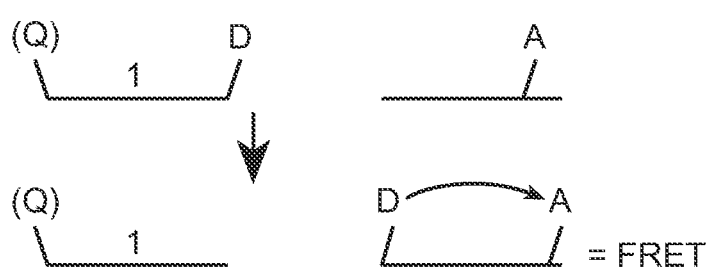

FIG. 14 is a schematic illustration of general embodiments of the transfer reaction. In panel A, ligation probe 1 comprises both a fluorophore (F) and a quencher molecule (Q) which are in close enough proximity for the quencher molecule to inhibit any signal from the fluorophore. Once ligation probe 1 and ligation probe 2 hybridize to adjacent/nearby positions on the target nucleic acid, the quencher molecule is "transferred" from ligation probe 1 to ligation probe 2, such that the quencher molecule is no longer able to inhibit or "quench" the fluorophore, and a signal can be detected.

In panel B, another configuration is pictured in which, rather than transfer of the quencher molecule, it is the fluorophore which is transferred upon hybridization of the ligation probes to adjacent/nearby positions on the target nucleic acid.

Panel C depicts another embodiment of the transfer reaction which utilizes Forster Resonance Energy Transfer (FRET) reactions. FRET involves an energy transfer mechanism between two chromophores. Although FRET is commonly called "Fluorescence" resonance energy transfer, it is not always detected with fluorescence. In this embodiment, each ligation probe comprises a chromophore (D and A). The donor (D) is excited at its specific excitation wavelength. Upon hybridization of the ligation probes to adjacent/nearby sites on the target nucleic acids, one of the chromophores is transferred to the other ligation probe, such that the donor (D) is near enough to the acceptor (A) to nonradiatively transfer an electron to the acceptor, returning the donor to its ground state. As a result, a signal will be detected at the acceptor's (A's) emission wavelength upon hybridization of the ligation probes in the proper configuration, but without that hybridization, there will no/very little signal at the emission wavelength of the acceptor molecule. Preferably, the donor and acceptor molecules will have emission wavelengths which are distinct enough from one another such that monitoring at the emission wavelength of one of the molecules would not detect emission from the other molecule. In the alternative, a ratio of the emission wavelengths can be measured, such that hybridization of the probes in the proper configuration and position will result in an increase of the emission wavelength signal of the acceptor over that of the donor.

Samples

Accordingly, the present invention provides compositions and methods for detecting the presence or absence of target sequences in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Some embodiments utilize siRNA and microRNA as target sequences (Zhang et al., *J Cell Physiol*. (2007) 210(2):279-89; Osada et al., *Carcinogenesis*. (2007) 28(1):2-12; and Mattes et al., *Am J Respir Cell Mol Biol*. (2007) 36(1):8-12, each of which is incorporated herein by reference in its entirety).

Some embodiments utilize nucleic acid samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage. Such samples are often not useful for traditional methods of nucleic acid detection, because such studies require a high integrity of the nucleic acid sample so that an accurate measure of nucleic acid expression can be made. Often, gene expression studies in paraffin-embedded samples are limited to qualitative monitoring by using immunohistochemical staining to monitor protein expression levels.

Methods and compositions of the present invention are particularly useful in detection of nucleic acids from paraffin-embedded samples, because the process of fixing and embedding in paraffin often results in degradation of the samples' nucleic acids. The present invention is able to amplify and detect even degraded samples, such as those found in paraffin-embedded samples. The sample nucleic acid can be either genomic or RNA, with mRNA and microRNA (or siRNA) being detectable using the present invention.

A number of techniques exist for the purification of nucleic acids from biological samples, but none is reliable for isolation of nucleic acids from fixed paraffin-embedded samples. For example, Chomczynski (U.S. Pat. No. 5,346,994; incorporated herein by reference in its entirety) describes a method for purifying RNA from tissues based on a liquid phase separation using phenol and guanidine isothiocyanate. A biological sample is homogenized in an aqueous solution of phenol and guanidine isothiocyanate and the homogenate thereafter mixed with chloroform. Following centrifugation, the homogenate separates into an organic phase, an interphase and an aqueous phase. Proteins are sequestered in the organic phase, DNA in the interphase, and RNA in the aqueous phase. RNA can be precipitated from the aqueous phase. Unfortunately, this method is not applicable to fixed and paraffin-embedded tissue samples.

Other known techniques for isolating nucleic acids typically utilize either guanidine salts or phenol extraction, as described for example in Sambrook, J. et al., *Molecular Cloning* (1989) at pp. 7.3-7.24, and in Ausubel, F. M. et al., *Current Protocols in Molecular Biology*, (1994) at pp. 4.0.3-4.4.7. Again, none of the known methods provides reproducible quantitative results in the isolation of RNA from paraffin-embedded tissue samples.

Techniques for the isolation of RNA and other nucleic acids from paraffin-embedded tissues are thus particularly needed for the study of gene expression such tissues, particularly in the diagnosis and prognosis of diseases such as cancer, since expression levels of certain receptors or enzymes can be used to determine the likelihood of success of a particular treatment.

In one embodiment, nucleic acids may be isolated from a paraffin-embedded sample which is first deparaffinized. An exemplary deparaffinization method involves washing the paraffinized sample with an organic solvent, such as xylene, for example. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration, for example. Alternatively, the sample is simultaneously deparaffinized and rehydrated. RNA is then extracted from the sample. Other methods known in the art may also be used to isolate nucleic acids from paraffin-embedded samples In a preferred embodiment, the target analytes are nucleic acids. By "nucleic acid" or "oligonucleotide" or grammatical equivalents herein means at least two nucleotides covalently linked together. A nucleic acid of the present invention will generally contain phosphodiester bonds (for example in the case of the target sequences), although in some cases, as outlined below, nucleic acid analogs are included that may have alternate backbones (particularly for use with the ligation probes), comprising, for example, phosphoramide (Beaucage et al., *Tetrahedron* (1993) 49(10):1925 and references therein; Letsinger, *J. Org. Chem*. (1970) 35:3800; Sprinzl et al., *Eur. J. Biochem*. (1977) 81:579; Letsinger et al., *Nucl. Acids Res*. (1986) 14:3487; Sawai et al, *Chem. Lett*. (1984) 805; Letsinger et al., *J. Am. Chem. Soc*. (1988) 110:4470; and Pauwels et al., *Chemica Scripta* (1986) 26:141), phosphorothioate (Mag et al., *Nucleic Acids Res*. (1991) 19:1437; and U.S. Pat. No. 5,644,048), phosphorodithioate (Briu et al., *J. Am. Chem. Soc*. (1989) 111:2321, O-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc*. (1992)114:1895; Meier et al., *Chem. Int. Ed. Engl*. (1992) 31:1008; Nielsen, *Nature*, (1993) 365:566; Carlsson et al., *Nature* (1996) 380:207, all of which are incorporated herein by reference in their entirety). Other analog nucleic acids include those with bicyclic structures including locked nucleic acids, Koshkin et al., *J. Am. Chem. Soc*. (1998) 120:13252 3); positive backbones (Denpcy et al., *Proc. Natl. Acad. Sci. USA* (1995) 92:6097; non-ionic backbones (U.S. Pat. Nos. 5,386,023, 5,637,684, 5,602,240, 5,216,141 and 4,469,863; Kiedrowshi et al., *Angew. Chem. Intl. Ed. English* (1991) 30:423; Letsinger et al., *J. Am. Chem. Soc*. (1988) 110:4470; Letsinger et al., *Nucleoside & Nucleotide* (1994) 13:1597; Chapters 2 and 3, *ASC Symposium Series* 580, Ed. Y. S. Sanghui and P. Dan Cook; Mesmaeker et al., *Bioorganic & Medicinal Chem. Lett*. (1994) 4:395; Jeffs et al., *J. Biomolecular NMR* (1994) 34:17; Xu et al., *Tetrahedron Lett*.

(1996) 37:743) and non-ribose backbones, including those described in U.S. Pat. Nos. 5,235,033 and 5,034,506, and Chapters 6 and 7, *ASC Symposium Series* 580, Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, *C & E News* Jun. 2, 1997 page 35. All of these references are herein expressly incorporated by reference. These modifications of the ribose-phosphate backbone may be done to facilitate the addition of labels or other moieties, to increase or decrease the stability and half-life of such molecules in physiological environments, etc.

As will be appreciated by those in the art, all of these nucleic acid analogs may find use in the present invention. In addition, mixtures of naturally occurring nucleic acids and analogs can be made; for example, at the site of a ligation moiety, an analog structure may be used. Alternatively, mixtures of different nucleic acid analogs, and mixtures of naturally occurring nucleic acids and analogs may be made.

Nucleic acid analogue includes, for example, peptide nucleic acid (PNA, WO 92/20702, incorporated herein by reference in its entirety) and Locked Nucleic Acid (LNA, Koshkin A A et al. *Tetrahedron* (1998) 54:3607-3630, Koshkin A A et al. *J. Am. Chem. Soc.* (1998) 120:13252-13253, Wahlestedt C et al. *PNAS* (2000) 97:5633-5638, each of which is incorporated herein by reference in its entirety). These find particular use in the invention as these backbones may exhibit improved hybridization kinetics, improved thermal stability and improved sensitivity to mismatch sequences.

The nucleic acids may be single stranded or double stranded, as specified, or contain portions of both double stranded or single stranded sequences. The nucleic acid may be DNA, both genomic and cDNA, RNA or a hybrid, where the nucleic acid contains any combination of deoxyribo- In one aspect, ligation probes of the invention are any polymeric species that is capable of interacting with a nucleic acid target(s) in a sequence specific manner and possess chemical moieties allowing the probes to undergo a spontaneous chemical ligation reaction with another polymeric species possessing complementary chemical moieties. In a preferred embodiment, the oligonucleotide probes can be DNA, RNA, PNA, LNA, modified versions of the aforementioned and/or any hybrids of the same (e.g. DNA/RNA hybrids, DNA/LNA hybrids, DNA/PNA hybrids). In a further preferred embodiment, the oligonucleotide probes are DNA oligonucleotides.

Nucleic acid samples (e.g. target sequences) that do not exist in a single-stranded state in the region of the target sequence(s) are generally rendered single-stranded in such region(s) prior to detection or hybridization. Generally, nucleic acid samples will be rendered single-stranded in the region of the target sequence using heat denaturation. For polynucleotides obtained via amplification, methods suitable for generating single-stranded amplification products are preferred. Non-limiting examples of amplification processes suitable for generating single-stranded amplification product polynucleotides include, but are not limited to, T7 RNA polymerase run-off transcription, RCA, Asymmetric PCR (Bachmann et al., *Nucleic Acid Res*. (1990) 18:1309), and Asynchronous PCR (WO 01/94638). Commonly known methods for rendering regions of double-stranded polynucleotides single stranded, such as the use of PNA openers (U.S. Pat. No. 6,265,166), may also be used to generate single-stranded target sequences on a polynucleotide.

In most embodiments, the ligation probes are single stranded.

The invention provides for methods of detecting target sequences. By "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA, MicroRNA and rRNA, or others. As is outlined herein, the target sequence may be a target sequence from a sample, or a secondary target such as a product of an amplification reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

As is outlined more fully below, probes are made to hybridize to target sequences to determine the presence or absence of the target sequence in a sample. Generally speaking, this term will be understood by those skilled in the art.

IN many embodiments, the target sequence may also be comprised of different target domains; for example, a first target domain of the sample target sequence may hybridize to a first ligation probe, and a second target domain may hybridize to a second ligation probe. Other target domains may hybridize to a capture probe on a substrate such as an array, a label probe, etc., as is more fully outlined herein.

The target domains may be adjacent or separated as indicated, as is more fully described below. In some cases, when detection is based on ligation and the application requires amplification of signal, the ligation probes may utilize linkers and be separated by one or more nucleobases of the target sequence to confer hybridization instability on the ligated product. In other applications, for example in single nucleotide polymorphism (SNP) detection, or in transfer reactions, the ligation probes may hybridize to adjacent nucleobases of the target sequence. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. For ease of reference and not to be limiting, these domains are sometimes referred to as "upstream" and "downstream", with the normal convention being the target sequence being displayed in a 5' to 3' orientation The probes are designed such that when the probes bind to a part of the target polynucleotide in close spatial proximity, a chemical ligation reaction occurs between the probes. In general, the probes comprise chemically reactive moieties (herein generally referred to as "ligation moieties") and bind to the target polynucleotide in a particular orientation, such that the chemically reactive moieties come into close spatial proximity, thus resulting in a spontaneous ligation reaction.

Probe Components

The invention provides sets of ligation probes, usually a first and a second ligation probe, although as is described herein some embodiments utilize more than two. In addition, as noted herein, in some cases a transfer reaction is done rather than ligation; "ligation probes" includes "transfer probes". Each ligation probe comprises a nucleic acid portion, sometimes referred to herein as a "probe domain" that is substantially complementary to one of the target domains. Probes of the present invention are designed to be complementary to a target sequence such that hybridization of the target sequence and the probes of the present invention occurs. As outlined herein, this complementarity need not be perfect; there may be any number of base pair mismatches which will interfere with hybridization between the target sequence and the probes of the present invention. However, if the number of mutations is so great that no hybridization can occur under even the least stringent of hybridization conditions, the sequence is not a complementary sequence. Thus, by "substantially complementary" herein is meant that the probes are sufficiently complementary to the target sequences to hybridize under normal reaction conditions. "Identical" sequences are those that over the length of the shorter sequence of nucleobases, perfect complementarity exists.

As is appreciated by those in the art, the length of the probe will vary with the length of the target sequence, the specificity required, the reaction (e.g. ligation or transfer) and the hybridization and wash conditions. Generally, ligation probes range from about 5 to about 75 nucleobases, with from about 10 to about 50 being preferred and from about 12 to about 35 being especially preferred. In general, these lengths apply equally to ligation and transfer probes A variety of hybridization conditions may be used in the present invention, including high, moderate and low stringency conditions; see for example Maniatis et al., *Molecular Cloning: A Laboratory Manual*, 2d Edition, 1989, and Ausubel, et al, *Short Protocols in Molecular Biology*, herein incorporated by reference. The hybridization conditions may also vary when a non-ionic backbone, e.g. *PNA is used, as is known in the art*.

Ligation Moieties

In addition to ligation domains, the ligation probes of the invention have ligation moieties. Accordingly, in one aspect, the invention describes methods of chemical ligation that include the binding of at least a first and a second ligation probe to the target nucleic acid to form a "ligation substrate" under conditions such that the ligation moieties of the first and second ligation probes react, ligating the probes together, in the absence of an enzymatic exogenous ligase; that is, no exogenous ligase is added to the reaction. In the case of the transfer reaction, this may be referred to as either a "ligation substrate" or a "transfer substrate". By "ligation substrate" herein is meant a substrate for chemical ligation comprising at least one target nucleic acid sequence and two or more ligation probes. Similarly, included within the definition of "ligation substrate" is a "transfer substrate", comprising at least one target nucleic acid sequence and two or more transfer probes.

In some embodiments, for example when additional specificity is desired, more than two ligation probes can be used. In this embodiment, the "middle" ligation probe(s) can also be adjacent or separated by one or more nucleobases of the target sequence. In a preferred embodiment, the ligation reaction does not require the presence of a ligase enzyme and occurs spontaneously between the bound probes in the absence of any addition (e.g. exogeneous) ligase.

Oligonucleotide probes of the invention are designed to be specific for the polynucleotide target. These probes bind to the target in close spatial proximity to each other and are oriented in such a manner that the chemically reactive moieties are in close spatial proximity. In one aspect, two or more probes are designed to bind near adjacent sites on a target polynucleotide. In a preferred embodiment, two probes bind to the target such that the 5' end of one oligonucleotide is able to interact with the 3' end of the other probe.

Chemical ligation can, under appropriate conditions, occur spontaneously without the addition of any additional activating reagents or stimuli. Alternatively, "activating" agents or external stimuli can be used to promote the chemical ligation reaction. Examples of activating agents include, without limitation, carbodiimide, cyanogen bromide (BrCN), imidazole, 1-methylimidazole/carbodiimide/cystamine, N-cyanoimidazole, dithiothreitol (DTT), tris(2-carboxyethyl)phosphine (TCEP) and other reducing agents as well as external stimuli like ultraviolet light, heat and/or pressure changes.

As is outlined herein, the ligation moieties of the invention may take a variety of configurations, depending on a number of factors. Most of the chemistries depicted herein are used in phosphoramidite reactions that generally progress in a 3' to 5' direction. That is, the resin contains chemistry allowing attachment of phosphoramidites at the 5' end of the molecule. However, as is known in the art, phosphoramidites can be used to progress in the 5' to 3' direction; thus, the invention includes moieties with opposite orientation to those outlined herein.

Each set of ligation probes (or transfer probes) contains a set of a first ligation moiety and a second ligation moiety. The identification of these ligation moiety pairs depends on the chemistry of the ligation to be used. In addition, as described herein, linkers (including but not limited to destabilization linkers) may be present between the probe domain and the ligation moiety of one or both ligation probes. In general, for ease of discussion, the description herein may use the terms "upstream" and "downstream" ligation probes, although this is not meant to be limiting.

Halo Leaving Group Chemistry

In one embodiment, the chemistry is based on 5' halogen leaving group technology such as is generally described in Gryanov, S. M., and Letsinger, R. L., (1993) *Nucleic Acids Research*, 21:1403; Xu, Y. and Kool, E. T. (1997) *Tetrahedron Letters*, 38:5595; Xu, Y. and Kool, E. T., (1999) *Nucleic Acids Research*, 27:875; Arar et al., (1995), *BioConj. Chem.*, 6:573; Kool, E. T. et. al, (2001) *Nature Biotechnol* 19:148; Kool, E. T. et. al., (1995) *Nucleic Acids Res*, 23 (17):3547; Letsinger et al., U.S. Pat. No. 5,476,930; Shouten et al., U.S. Pat. No. 6,955,901; Andersen et al., U.S. Pat. No. 7,153,658, all of which are expressly incorporated by reference herein. In this embodiment, the first ligation includes at its 5' end a nucleoside having a 5' leaving group, and the second ligation probe includes at its 3' end a nucleoside having 3' nucleophilic group such as a 3' thiophosphoryl. The 5' leaving group can include many common leaving groups obvious to those skilled in the art especially halo-species (I, Br, Cl) and groups such as those described by Abe and Kool, *J. Am. Chem. Soc.* (2004) 126:13980-13986, which is incorporated herein by reference in its entirety. In a more preferred embodiment, the first ligation probe has a 5' leaving group attached through a flexible linker and a downstream oligonucleotide which has a 3' thiophosphoryl group. This configuration leads to a significant increase in the rate of reaction and results in multiple copies of ligated product being produced for every target.

The "upstream" oligonucleotide, defined in relation to the 5' to 3' direction of the polynucleotide template as the oligonucleotide that binds on the "upstream" side (i.e., the left, or 5' side) of the template includes, as its 5' end, a 5'-leaving group. Any leaving group capable of participating in an $S_N2$ reaction involving sulfur, selenium, or tellurium as the nucleophile can be utilized. The leaving group is an atom or group attached to carbon such that on nucleophilic attack of the carbon atom by the nucleophile (sulfur, selenium or tellurium) of the modified phosphoryl group, the leaving group leaves as an anion. Suitable leaving groups include, but are not limited to a halide, such as iodide, bromide or chloride, a tosylate, benzenesulfonate or p-nitrophenylester, as well as $RSO_3$ where R is phenyl or phenyl substituted with one to five atoms or groups comprising F, Cl, Br, I, alkyl (C1 to C6), nitro, cyano, sulfonyl and carbonyl, or R is alkyl with one to six carbons. The leaving group is preferably an iodide, and the nucleoside at the 5' end of the upstream oligonucleotide is, in the case of DNA, a 5'-deoxy-5'-iodo-2'-deoxynucleoside. Examples of suitable 5'-deoxy-5'-iodo-2'-deoxynucleosides include, but are not limited to, 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof (see FIG. 2). In the case of RNA oligonucleotides, analogous examples of suitable 5'-deoxy-5'-iodonucleosides include, but are not limited to, 5'-deoxy-5'-iodouracil (5'-I-U), 5'-deoxy-5'-iodocytidine (5'-I-C), 5'-deoxy-5'-iodoadenosine (5'-I-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof In a preferred embodiment, an upstream ligation probe contains 2'-deoxyribonucleotides except that the modified nucleotide on the 5' end, which comprises the 5' leaving group, is a ribonucleotide. This embodiment of the upstream nucleotide is advantageous because the bond between the penultimate 2'-deoxyribonucleotide and the terminal 5' ribonucleotide is susceptible to cleavage using base. This allows for potential reuse of an oligonucleotide probe that is, for example, bound to a solid support, as described in more detail below.

The "downstream" oligonucleotide, which binds to the polynucleotide template "downstream" of, i.e., 3' to, the upstream oligonucleotide, includes, as its 3' end, a nucleoside having linked to its 3' hydroxyl a phosphorothioate group (i.e., a "3'-phosphorothioate group"), a phosphoroselenoate group (i.e., a "3'-phosphoroselenoate group), or a phosphorotelluroate group (i.e., a "3'-phosphorotelluroate group"). The chemistries used for autoligation are thus sulfur-mediated, selenium-mediated, or tellurium mediated. Self-ligation yields a ligation product containing a 5' bridging phosphorothioester (—O—P(O)(O.sup.-)-S—), phosphoroselenoester (—O—P(O)(O.sup.-)-Se—) or phosphorotelluroester (—O—P(O)(O.sup.-)-Te—), as dictated by the group comprising the 3' end of the downstream oligonucleotide. This non-natural, achiral bridging diester is positioned between two adjacent nucleotides and takes the place of a naturally occurring 5' bridging phosphodiester. Surprisingly, the selenium-mediated ligation is 3 to 4 times faster than the sulfur-mediated ligation, and the selenium-containing ligation product was very stable, despite the lower bond strength of the Se—P bond. Further, the bridging phosphoroselenoester, as well as the bridging phosphorotelluroester, are expected to be cleavable selectively by silver or mercuric ions under very mild conditions (see Mag et al., *Nucleic Acids Res*. (1991) 19:1437 1441).

In one embodiment, a downstream oligonucleotide contains 2'-deoxyribonucleotides except that the modified nucleotide on the 3' end, which comprises the 3' phosphorothioate, phosphoroselenoate, or phosphorotelluroate, is a ribonucleotide. This embodiment of the upstream nucleotide is advantageous because the bond between the penultimate 2'-deoxyribonucleotide and the terminal ribonucleotide is susceptible to cleavage using base, allowing for potential reuse of an oligonucleotide probe that is, for example, bound to a solid support.

It should be noted that the "upstream" and "downstream" oligonucleotides can, optionally, constitute the two ends of a single oligonucleotide, in which event ligation yields a circular ligation product. The binding regions on the 5' and 3' ends of the linear precursor oligonucleotide must be linked by a number of intervening nucleotides sufficient to allow binding of the 5' and 3' binding regions to the polynucleotide target.

Compositions provided by the invention include a 5'-deoxy-5-'iodo-2'-deoxynucleoside, for example a 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof, as well as an oligonucleotide comprising, as its 5' end, a 5'-deoxy-5'-iodo-2'-deoxynucleoside of the invention. Compositions provided by the invention further include a 5'-deoxy-5'-iodonucleoside such as 5'-deoxy-5'-iodouracil (5'-I-U), 5'-deoxy-5'-iodocytidine (5'-I-C), 5'-deoxy-5'-iodoadenosine (5'-1-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof, as well as an oligonucleotide comprising, as its 5' end, a 5'-deoxy-5'-iodonucleoside of the invention. Also included in the invention is a nucleoside comprising a 3'-phosphoroselenoate group or a 3'-phosphorotelluroate group, and an oligonucleotide comprising as its 3' end a nucleoside comprising a 3'-phosphoroselenoate group or a 3'-phosphorotelluroate group. Oligonucleotides containing either or both of these classes of modified nucleosides are also included in the invention, as are methods of making the various nucleosides and oligonucleotides. Oligonucleotides that are modified at either or both of the 5' or 3' ends in accordance with the invention optionally, but need not, include a detectable label, preferably a radiolabel, a fluorescence energy donor or acceptor group, an excimer label, or any combination thereof.

Native Peptide Ligation

Figure 4:
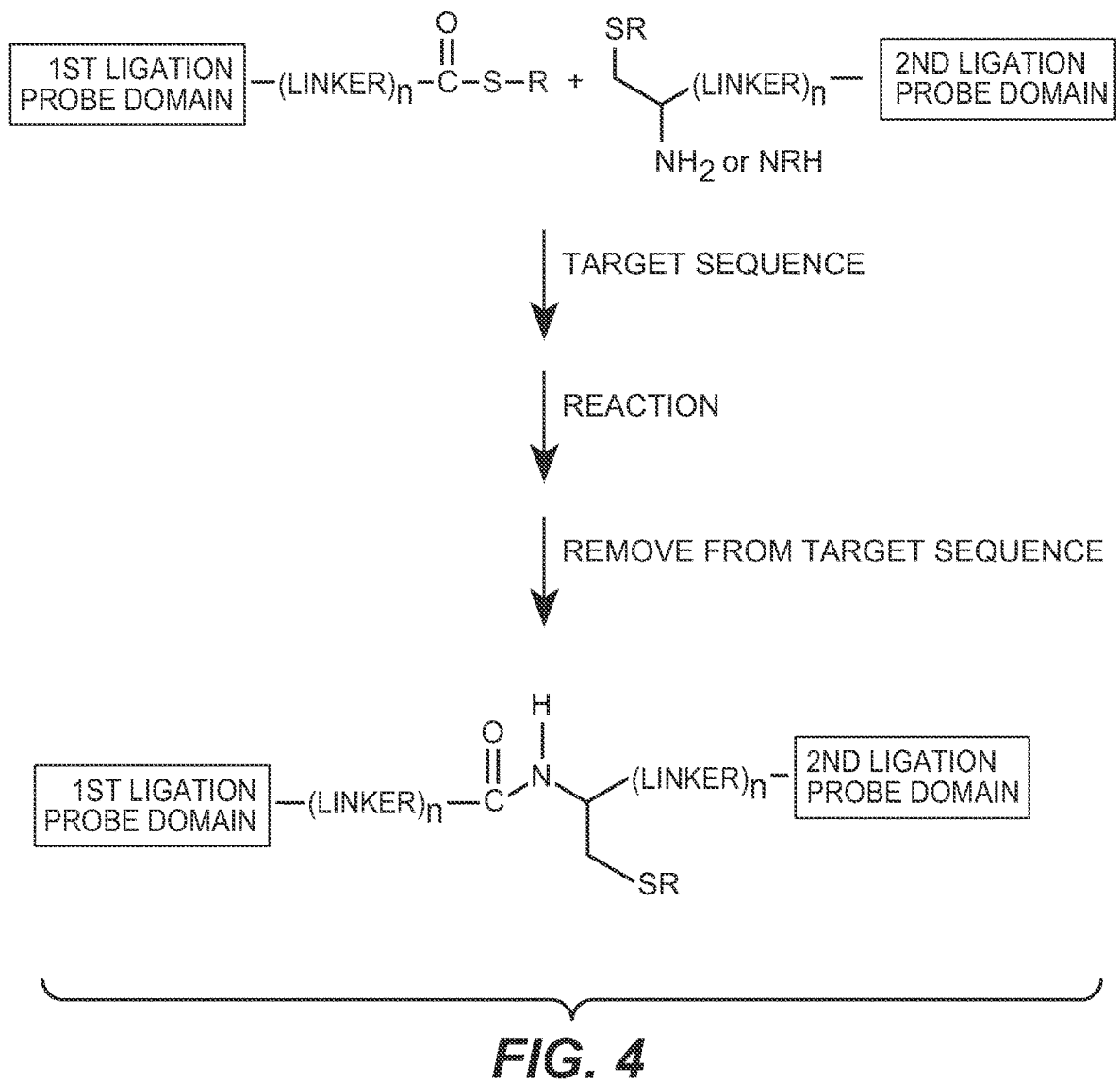
FIG. 4 depicts a generic schematic native peptide ligation as applied to nucleic acids.

In one embodiment, thioester linkage technology is used for the chemical ligation reaction. This chemistry, sometimes referred to as "native peptide ligation" (NPL) as described Ficht et al., *J. Am. Chem. Soc.* (2004) 126:9970-9981; Dose et al., *Org. Letters* (2005) 7:20 4365-4368 Ficht et al., *ChemBioChem* (2005) 6:2098-2103; Dose et al., *Angew. Chem. Int. Ed*, (2006) 45:5369-5373; Grossman et al., *J. Am. Chem. Soc.* (2006) 128: 15596-15597; all of which are expressly incorporated by reference herein, relies on the use of thioester replacement by nitrogen containing groups to result in amide linkages. The general reaction is depicted in FIG. 4. NPL has been extensively utilized for the construction of synthetic peptides and proteins, and was recently utilized to join PNA oligomers (Dose 2006). While significant work has gone into developing methodologies and reagents for peptide synthesis, there are limited examples of developing native peptide ligation reagents for automated DNA synthesis, and no example of reagents for incorporating a thioester moiety into DNA using automated DNA synthesis.

A significant hurdle to the incorporation of a thioester moiety via automated DNA synthesis is the limited stability of the thioester group in a basic pH. As is more fully described below, the present invention provides a solution to this limited stability by providing reagents that can be used to insert a masked thioester moiety via automated DNA synthesis, which, following deprotection, can generate a thioester group, the reactive species in the ligation reaction. These thioester reagents can be used in conjunction with other nucleophilic groups to ligate oligonucleotide fragments together. The reagents further comprise moieties to allow them to be used in conjunction with a wide variety of phosphoramidite labeling reagents, such as those described in the Glen Research Product catalog, thus producing labeled probes that can either ligate with another molecule or transfer a label to another molecule via chemical ligation chemistry. The protected ligation moieties and methods of generating and deprotecting them are described below.

Thioester Ligation Moieties

In this embodiment, one of the ligation probes comprises a thioester ligation moiety. By "thioester" herein is meant a —(CO)—SR moiety, as depicted in the figures. In many embodiments, the thioester ligation moiety is present near or at the 3' of the "downstream" ligation probe For ease of discussion, the thioester ligation moiety is depicted herein as a component of the "downstream" ligation probe; however, the ligation moieties of this embodiment may be switched.

The R moiety may be any substituent group. In general, suitable "R" substituent groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different, independently selected from suitable substituent groups; in this embodiment, one R may be hydrogen. In addition, R groups on adjacent carbons may also form ring structures, including cycloalkyl and aryl rings. In some embodiments, as is more fully outlined below, the R group attached to a leaving group (such as in the thioester configurations of —(CO)—SR depicted below) is a functional R group, such as a quencher, a fluorophore, biotin, for either ligation or transfer reactions. In some embodiments, the term "substituent" may not include hydrogen.

In addition, in some cases, substituent groups may also be protecting groups (sometimes referred to herein as "PG"). Suitable protecting groups will depend on the atom to be protected and the conditions to which the moiety will be exposed. A wide variety of protecting groups are known; for example, DMT is frequently used as a protecting group in phosphoramidite chemistry (as depicted in the figures; however, DMT may be replaced by other protecting groups in these embodiments. A wide variety of protecting groups are suitable; see for example, Greene's Protective Groups in Organic Synthesis, herein incorporated by reference for protecting groups and associated chemistry.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about 01 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant $NH_2$, —NHR and —$NR_2$ groups, with R being as defined herein. In some embodiments, for example in the case of the peptide ligation reactions, primary and secondary amines find particular use, with primary amines generally showing faster reaction rates.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). A particular type of sulfur containing moiety is a thioester (—(CO)—S—), usually found as a substituted thioester (—(CO)—SR). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2$ $CH_3$ and —O—$(CH_2)_4$ $CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCOH groups.

By "alcohol" herein is meant —OH groups, and alkyl alcohols —ROH.

By "amido" herein is meant —RCONH— or RCONR— groups.

By "ethylene glycol" herein is meant a —(O—$CH_2$—$CH_2)_n$— group, although each carbon atom of the ethylene group may also be singly or doubly substituted, i.e. —(O—$CR_2$—$CR_2)_n$—, with R as described above. Ethylene glycol derivatives with other heteroatoms in place of oxygen (i.e. —(N—$CH_2$—$CH_2)_n$— or —(S—$CH_2$—$CH_2)_n$—, or with substitution groups) are also preferred.

Additionally, in some embodiments, the R group may be a functional group, including quenchers, destabilization moieties and fluorophores (as defined below). Fluorophores of particular use in this embodiment include, but are not limited to Fluorescein and its derivatizes, TAMRA (Tetramethyl-6-carboxyrhodamine), Alexa dyes, and Cyanine dyes (Cy3 and Cy5

Quencher moieties or molecules are known in the art, and are generally aromatic, multiring compounds that can deactivate the excited state of another molecule. Fluorophore-quencher pairs are well known in the art. Suitable quencher moieties include, but are not limited to Dabsyl (Dimethylamini(azobenzene) sulfonyl) Dabcyl (Dimethylamino (azobenzene)carbonyl), Eclipse Quenchers (Glen Research Catalog) and blackhole Quenchers (BHQ-1, BHQ-2 and BHQ-3) from Biosearch Technologies.

Suitable destabilization moieties are discussed below and include, but are not limited to molecule entities that result in a decrease in the overall binding energy of an oligonucleotide to its target site. Potential examples include, but are not limited to alkyl chains, charged complexes, and ring structures.

Nucleophile Ligation Moieties

In this embodiment, the other ligation probe comprises a ligation moiety comprising a nucleophile such as an amine. Ligation moieties comprising both a thiol and an amine find particular use in certain reactions. In general, the nucleophile ligation moieites can include a wide variety of potential amino, thiol compounds as long as the nucleophile ligation moiety contains a thiol group that is proximal to a primary or secondary amino and the relative positioning is such that at least a 5 or 6 member ring transition state can be achieve during the S to N acyl shift. In some cases, for example as depicted in the Figures, additional carbon atoms (substituted or not) that would form 7 or higher membered ring structures are acceptable, although a loss in reaction time may be seen.

Accordingly, nucleophile ligation molecules that comprise 1, 2 or 1, 3 amine thiol groups find particular use. Primary amines find use in some embodiments when reaction time is important, as the reaction time is generally faster for primary than secondary amines, although secondary amines find use in acyl transferase reactions that contribute to destabilization as discussed below. The carbons between the amino and thiol groups can be substituted with non-hydrogen R groups, although generally only one non-hydrogen R group per carbon is utilized. Additionally, adjacent R groups (depicted as R' and R" in FIG. 7) may be joined together to form cyclic structures, including substituted and unsubstituted cycloalkyl and aryl groups, including heterocycloalkyl and heteroaryl and the substituted and unsubstituted derivatives thereof. In the case where a 1,2 amino thiol group is used and adjacent R groups are attached, it is generally preferred that the adjacent R groups form cycloalkyl groups (including heterocycloalkyl and substituted derivatives thereof) rather than aryl groups.

In this embodiment, for the generation of the 4 sigma bond contraction of the chain for destabilization, the replacement ligation moiety relies on an acyl transferase reaction, as is generally depicted in the figures.

Linkers

In many embodiments, linkers (sometimes shown herein as "L" or "-(linker)$_n$-), (where n is zero or one) may optionally be included at a variety of positions within the ligation probe(s). Suitable linkers include alkyl and aryl groups, including heteroalkyl and heteroaryl, and substituted derivatives of these. In some instances, for example when NPL reactions are done, the linkers may be amino acid based and/or contain amide linkages. As described herein, some linkers allow the ligation probes to be separated by one or more nucleobases, forming abasic sites within the ligation product, which serve as destabilization moieties, as described below.

Destabilization Moieties

In accordance with the invention, it is desirable to produce multiple copies of ligated product for each target molecule without the aid of an enzyme. In order to achieve this goal, the ligated product should disassociate following the chemical ligation reaction and allow a new probe set to bind to the target. To thus increase product turnover, probe designs, instrumentation, and chemical ligation reaction chemistries that minimize product inhibition and increase product disassociation from the target molecule are needed.

Previous work has shown one way to achieve product disassociation and increase product turnover is to "heat cycle" the reaction mixture. Heat cycling is the process of varying the temperature of a reaction so as to facilitate a desired outcome. Most often heat cycling takes the form of briefly raising the temperature of the reaction mixture so that the reaction temperature is above the melting temperature of the ligated product for a brief period of time causing the product to disassociate from the target. Upon cooling, a new set of probes is able to bind the target, and undergo another ligation reaction. This heat cycling procedure has been practiced extensively for enzymatic reactions like PCR.

While heat cycling is one way to achieve product turnover, it is possible to design probes such that there is significant product turnover without heat cycling. Probe designs and ligation chemistries that help to lower the melting temperature of the ligated product increase product turnover by decreasing product inhibition of the reaction cycle.

Accordingly, in one aspect, for instance with ligation reactions, the probes are further designed to include elements (e.g. destabilization moieties), which, upon ligation of the probes, serve to destabilize the hybridization of the ligation product to the target sequence. As a result, the ligated substrate disassociates after ligation, resulting in a turnover of the ligation product, e.g. the ligation product comprising the two ligation probes dehybridizes from the target sequence, freeing the target sequence for hybridization to another probe set.

In addition, increasing the concentration of the free (e.g. unhybridized) ligation probes can also help drive the equilibrium towards release of the ligation product (or transfer product) from the target sequence. Accordingly, some embodiments use concentrations of probes that are 1,000,000 fold higher than that of the target while in other embodiments the probes are 10,000 to 100 fold higher than that of the target. As will be appreciated by those in the art, increasing the concentration of free probes can be used by itself or with any embodiment outlined herein to achieve product turnover (e.g. amplification). While increasing the probe concentration can result in increased product turnover, it can also lead to significant off target reactions such as probe hydrolysis and non-target mediated ligation.

In one aspect, these probe elements include structures which lower the melting temperature of the ligated product. In some embodiments, these probe elements are designed to hybridize to non-adjacent target nucleobases, e.g. there is a "gap" between the two hybridized but unligated probes. In general, this is done by using one or two linkers between the probe domain and the ligation moiety. That is, there may be a linker between the first probe domain and the first ligation moiety, one between the second probe domain and the second ligation moiety, or both. In some embodiments, the gap comprises a single nucleobase, although more can also be utilized as desired. As will be appreciated by those in the art, there may be a tradeoff between reaction kinetics and length of the linkers; if the length of the linker(s) are so long that contact resulting in ligation is kinetically disfavored, shorter linkers may be desired. However, in some cases, when kinetics are not important, the length of the gap and the resulting linkers may be longer, to allow spanning gaps of 1 to 10 nucleobases. Generally, in this embodiment, what is important is that the length of the linker(s) roughly corresponds to the number of nucleobases in the gap.

In one embodiment, the formation of abasic sites in a ligation product as compared to the target sequence serves to destabilize the duplex. For example, Abe and Kool (*J. Am. Chem. Soc.* (2004) 126:13980-13986) compared the turnover when two different 8-mer oligonucleotide probes (Bu42 and DT40) were ligated with the same 7-mer probe (Thio 4). When Thio4 is ligated with DT40, a continuous 15-mer oligonucleotide probe with a nearly native DNA structure is formed that should be perfectly matched with the DNA target. However, when Thio4 is ligated with Bu42, a 15-mer oligonucleotide probe is formed, but when the probe is bound to the target, it has an abasic site in the middle that is spanned by an alkane linker. Comparison of the melting temperature (Tm) of these two probes when bound to the target shows approximately a 12° C. difference in melting temperature (58.5 for Bu42 versus 70.7° C. for DT40). This 12° C. difference in melting temperature led to roughly a 10-fold increase in product turnover (91.6-Bu42 versus 8.2 DT40) at 25° C. when the probe sets (10,000-fold excess, 10 µM conc) were present in large excess compared to the target (1 nM). Similarly, Dose et al (Dose 2006) showed how a 4° C. decrease in Tm for two identical sequence, chemically ligated PNA probes (53° C. versus 57° C.) results in approximately a 4-fold increase in product turnover.

In one embodiment, destabilization moieties are based on the removal of stabilization moieties. That is, if a ligation probe contains a moiety that stabilizes its hybridization to the target, upon ligation and release of the stabilization moiety, there is a drop in the stability of the ligation product. Accordingly, one general scheme for reducing product inhibition is to develop probes that release a molecular entity like a minor groove binding molecule during the course of the initial chemical ligation reaction or following a secondary reaction post ligation. Depending on the oligonucleotide sequence, minor groove binders like the dihydropyrroloindole tripeptide (DPI$_3$) described by Kutyavin (Kutyavin 1997 and Kutyavin 2000) can increase the Tm of a duplex nucleic acid by up to 40° C. when conjugated to the end of an oligonucleotide probe. In contrast, the unattached version of the DPI3 only increases the Tm of the same duplex by 2° C. or so. Thus, minor groove binders can be used to produce probe sets with enhanced binding strengths, however if the minor groove binder is released during the course of the reaction, the binding enhancement is loss and the ligated product will display a decreased Tm relative to probes in which the minor groove binder is still attached.

Suitable minor groove binding molecules include, but are not limited to, dihydropyrroloindole tripeptide (DPI$_3$), distamycin A, and pyrrole-imidazole polyamides (Gottesfeld, J. M., et al., *J. Mol. Biol.* (2001) 309:615-629.

In addition to minor groove binding molecules tethered intercalators and related molecules can also significantly increase the melting temperature of oligonucleotide duplexes, and this stabilization is significantly less in the untethered state. (Dogan, et al., *J. Am. Chem Soc.* (2004) 126:4762-4763 and Narayanan, et al., *Nucleic Acids Research*, (2004) 32:2901-2911).

Similarly, as will be appreciated by those in the art, probes with attached oligonucleotide fragments (DNA, PNA, LNA, etc) capable of triple helix formation, can serve as stabilization moieties that upon release, results in a decrease of stabilization of the ligation product to the target sequence (Pooga, M, et al., *Biomolecular Engineering* (2001) 17:183-192.

Another general scheme for decreasing product inhibition by lowering the binding strength of the ligated product is to incorporate abasic sites at the point of ligation. This approach has been previously demonstrated by Abe (*J. Am. Chem. Soc.* (2004) 126:13980-13986), however it is also possible to design secondary probe rearrangements to further amplify the decrease in Tm via straining the alignment between the ligated probes and the target. For example, Dose et al. (*Org. Letters* (2005) 7:20 4365-4368) showed how a rearrangement post-ligation that changed the spacing between PNA bases from the ideal 12 sigma bonds to 13 resulted in a lowering of the Tm by 4° C. Larger rearrangements and secondary reactions that interfere with the binding of the product to the target or result in the loss of oligonucleotide bases can further decrease the Tm.

Figure 5:
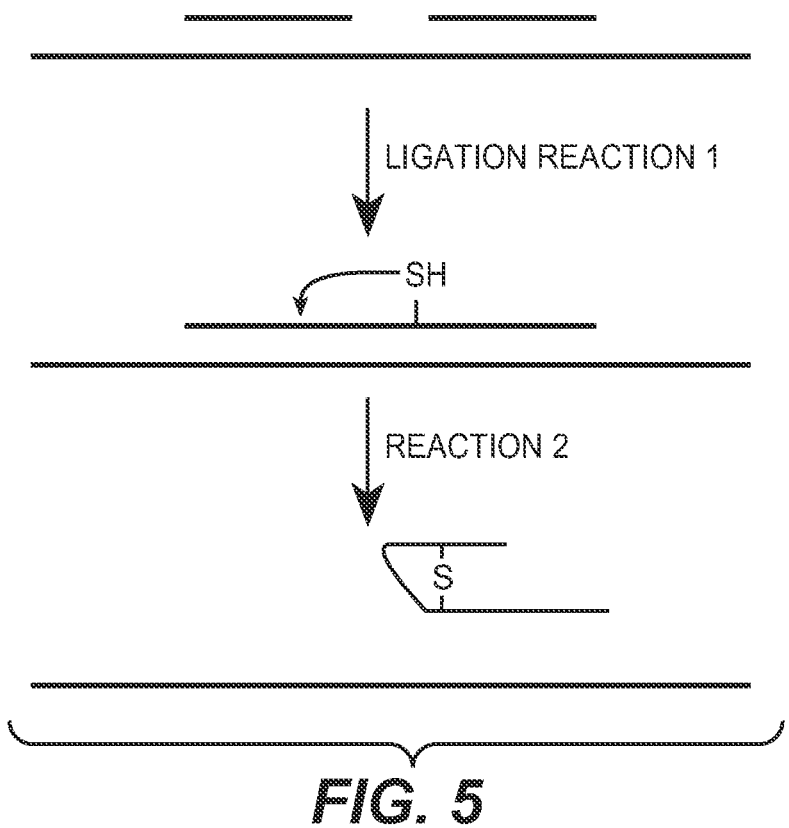
FIG. 5 depicts a secondary reaction of the FIG. 4 reaction, where the thiol (e.g. where the —SR group of FIG. 4 is —SH) binds to a moiety within the ligation product, forming a further "kink" and destabilizing the ligation product.
Figure 6:
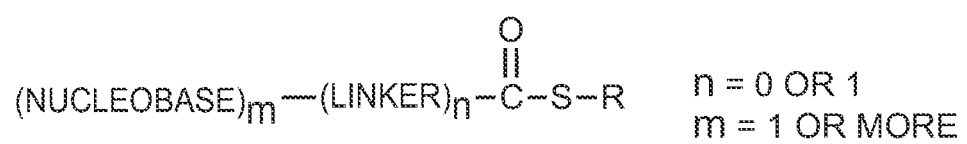
FIG. 6 depicts a standard NPL thioester containing ligation probe.
Figure 7:
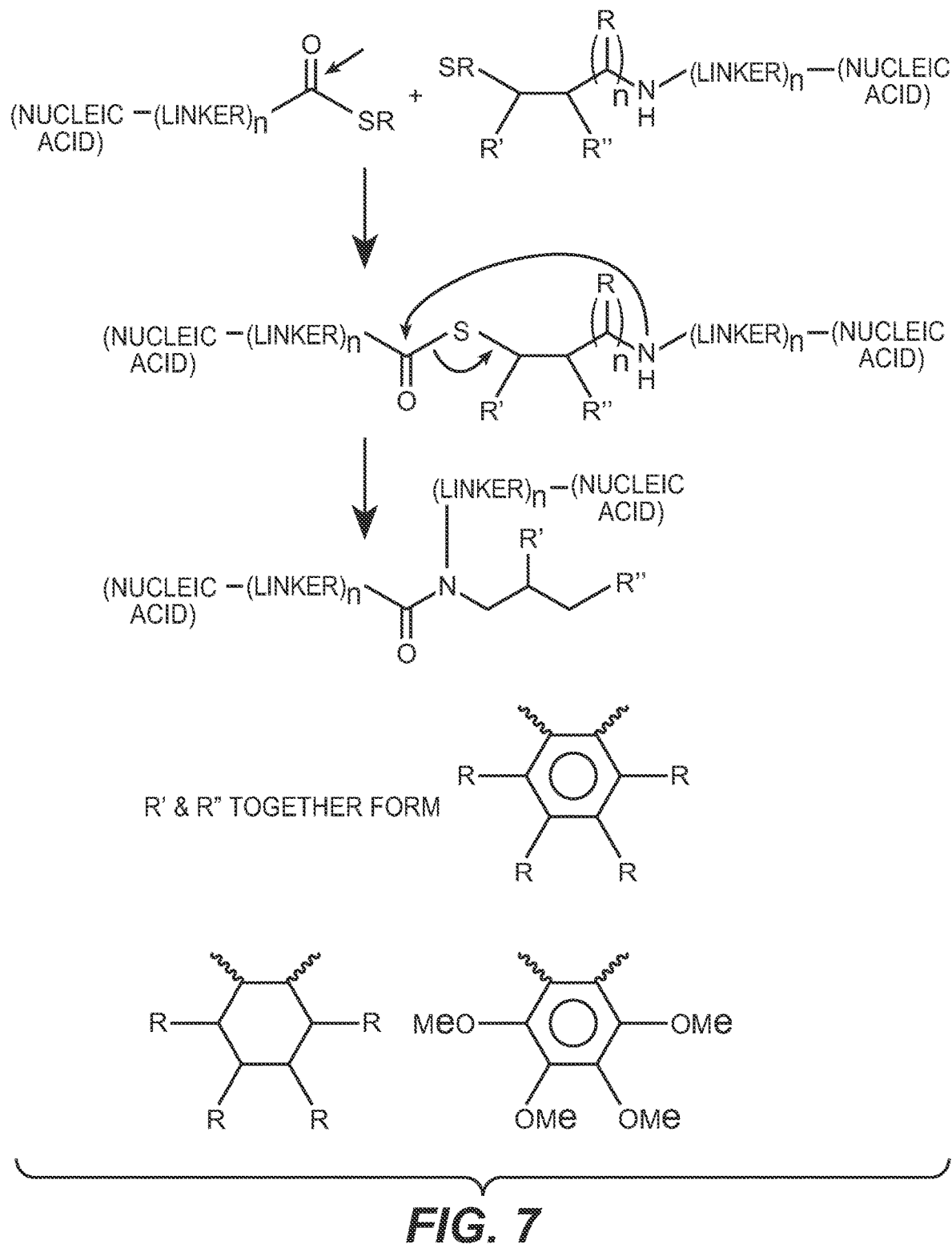
FIG. 7 depicts a schematic of an acyl transferase thioester reaction, that results in a chain reduction upon the secondary reaction resulting in further destabilization.
Figure 8:
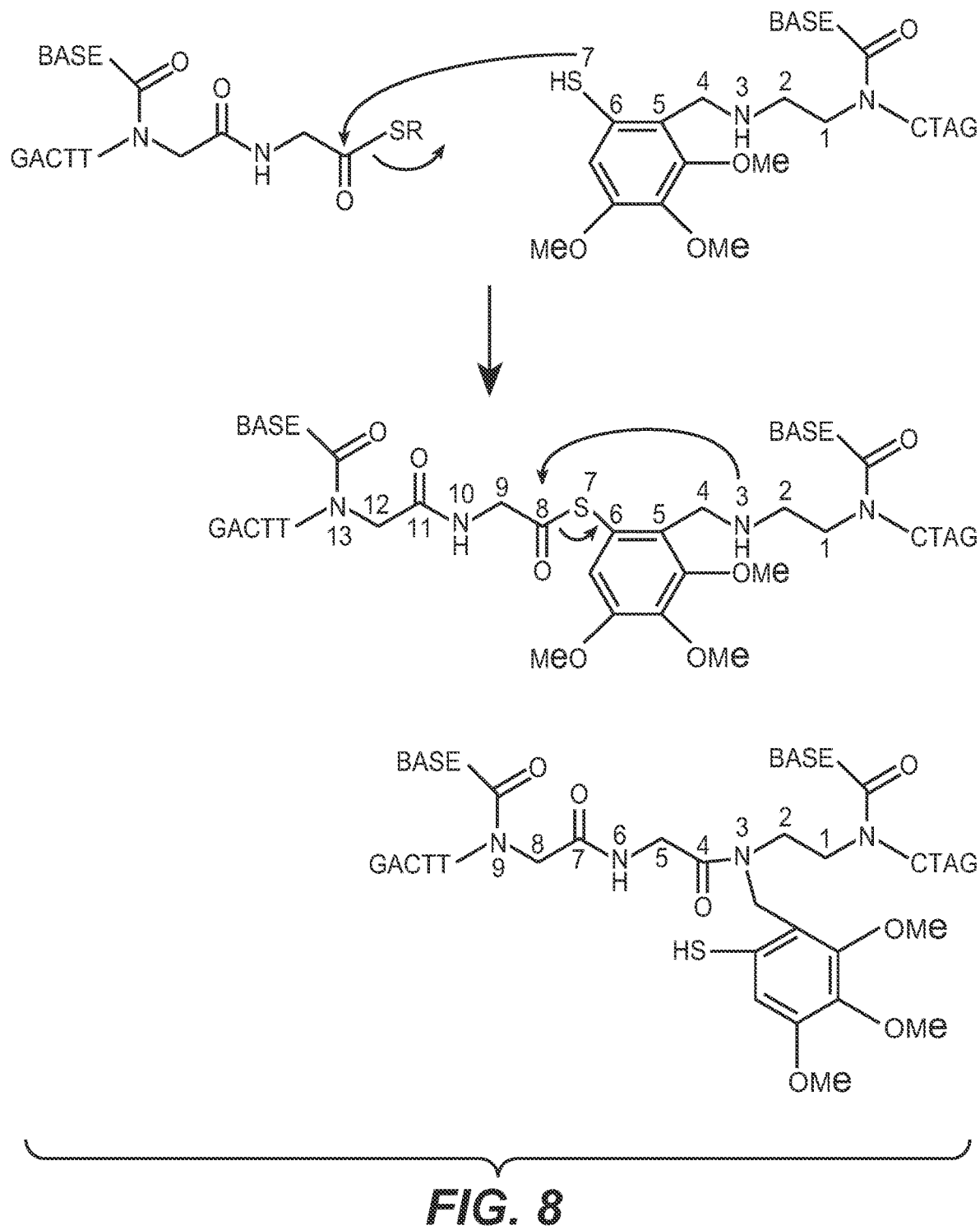
FIG. 8 depicts a preferred reaction of the scheme of FIG. 7.

The present invention provides methods and compositions for a ligation reaction that results in a chain contraction of up to 4 sigma bonds during the rearrangement, which should have a significant effect on the Tm post-rearrangement compared to the 1 base expansion using the chemistry described by Dose (FIG. 7 and FIG. 8). This chemistry is based on the acyl transfer auxiliary that has been described previously (Offer et al., *J Am Chem Soc.* (2002) 124(17): 4642-6). Following completion of the chain contraction, a free-thiol is generated that is capable of undergoing another reaction either with a separate molecule or with itself. For example, this thiol could react with an internal thioester to severely kink the oligonucleotide and thus further decrease the ligation product's ability to bind to the target (FIG. 5).

Thus, in this embodiment, ligation reactions that release functional groups that will undergo a second reaction with the ligation product can reduce stabilization of the hybrid of the ligation product and the target sequence.

Additional Functionalities of Ligation Probes

In addition to the target domains, ligation moieties, and optional linkers, one or more of the ligation probes of the invention can have additional functionalities, including, but not limited to, promoter and primer sequences (or complements thereof, depending on the assay), labels including label probe binding sequences, anchor sequences.

In one aspect of the invention, the upstream oligonucleotide can have a promoter site or primer binding site for a subsequent enzymatic amplification reaction. In a preferred embodiment, the upstream oligonucleotide contains the promoter sequence for a RNA polymerase, e.g. T7, SP6 or T3. In another embodiment, both the upstream and down stream oligonucleotides contain primer binding sequences. Promoter and primer binding sequences are designed so as to not interact with the nucleic acid targets to any appreciable extent. In a preferred embodiment, when detecting multiple targets simultaneously, all of the oligonucleotide probe sets in the reaction are designed to contain identical promoter or primer pair binding sites such that following ligation and appropriate clean-up, all of the ligated products can be amplified simultaneously using the same enzyme and/or same primers.

In one embodiment, one or more of the ligation probes comprise a promoter sequence. In embodiments that employ a promoter sequence, the promoter sequence or its complement will be of sufficient length to permit an appropriate polymerase to interact with it. A promoter is an expression control element that permits binding of polymerase and amplification of the target nucleic acid to occur. Generally, the promoter sequence permits binding of an RNA polymerase, thus allowing transcription of a target DNA molecule to occur. Detailed descriptions of sequences that are sufficiently long for polymerase interaction can be found in, among other places, Sambrook and Russell. In certain embodiments, amplification methods comprise at least one cycle of amplification, for example, but not limited to, the sequential procedures of: interaction of a polymerase with a promoter; synthesizing a strand of nucleotides in a template-dependent manner using a polymerase; and denaturing the newly-formed nucleic acid duplex to separate the strands.

In one embodiment, one or more of the ligation probes comprise a primer sequence. As is outlined below, the ligation products of the present invention may be used in additional reactions such as amplification reactions. In one embodiment, the ligation probes comprise primer sequences designed to allow an additional level of amplification. As used herein, the term "primer" refers to nucleotide sequence, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. One or more of the nucleotides of the primer can be modified, for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand.

By using several priming sequences and primers, a first ligation product can serve as the template for additional ligation products. These primer sequences may serve as priming sites for PCR reactions, which can be used to amplify the ligation products. In addition to PCR reactions, other methods of amplification can utilize the priming sequences, including but not limited to ligase chain reactions, Invader™, positional amplification by nick translation (NICK), primer extension/nick translation, and other methods known in the art. As used herein, "amplification" refers to an increase in the number of copies of a particular nucleic acid. Copies of a particular nucleic acid made in vitro in an amplification reaction are called "amplicons" or "amplification products".

Amplification may also occur through a second ligation reaction, in which the primer sites serve as hybridization sites for a new set of ligation probes which may or may not comprise sequences that are identical to the first set of ligation probes that produced the original ligation products. The target sequence is thus exponentially amplified through amplification of ligation products in subsequent cycles of amplification.

In one embodiment, the primer sequences are used for nested ligation reactions, additionally described below. In such nested ligation reactions, a first ligation reaction is accomplished using methods described herein such that the ligation product can be captured, for example by using biotinylated primers to the desired strand and beads (particularly magnetic beads) coated with streptavidin. After the ligation products are captured, a second ligation reaction is accomplished by hybridization of ligation probes to primer sequences within a section of the ligation product which is spatially removed from (i.e., downstream from) the end of the ligation product which is attached to the capture bead, probe, etc. At least one of the primer sequences for the secondary ligation reaction will be located within the region of the ligation product complementary to the ligation probe which is not the ligation probe that included the anchor or capture sequence. The ligation products from this second ligation reaction will thus necessarily only result from those sequences successfully formed from the first chemical ligation, thus removing any "false positives" from the amplification reaction. In another embodiment, the primer sequences used in the secondary reaction may be primer sites for other types of amplification reactions, such as PCR.

In one embodiment, one or more of the ligation probes comprise an anchor sequence. By "anchor sequence" herein is meant a component of ligation probe as defined herein that allows the attachment of a ligation product to a support for the purposes of detection. Generally, such an attachment will occur via hybridization of the anchor sequence with a capture probe, which is substantially complementary to the anchor sequence.

Figure 2A:
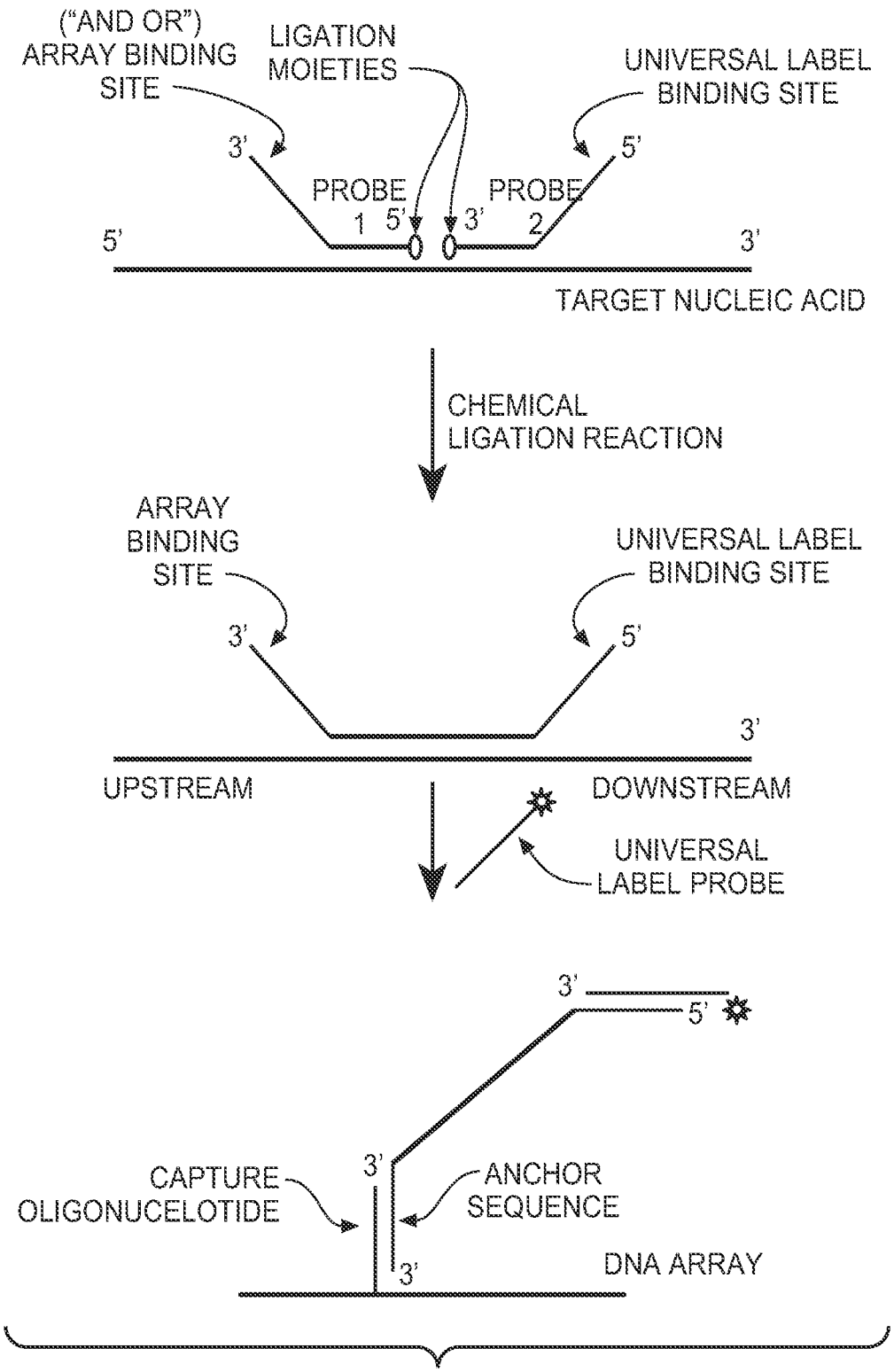
Figure 3:
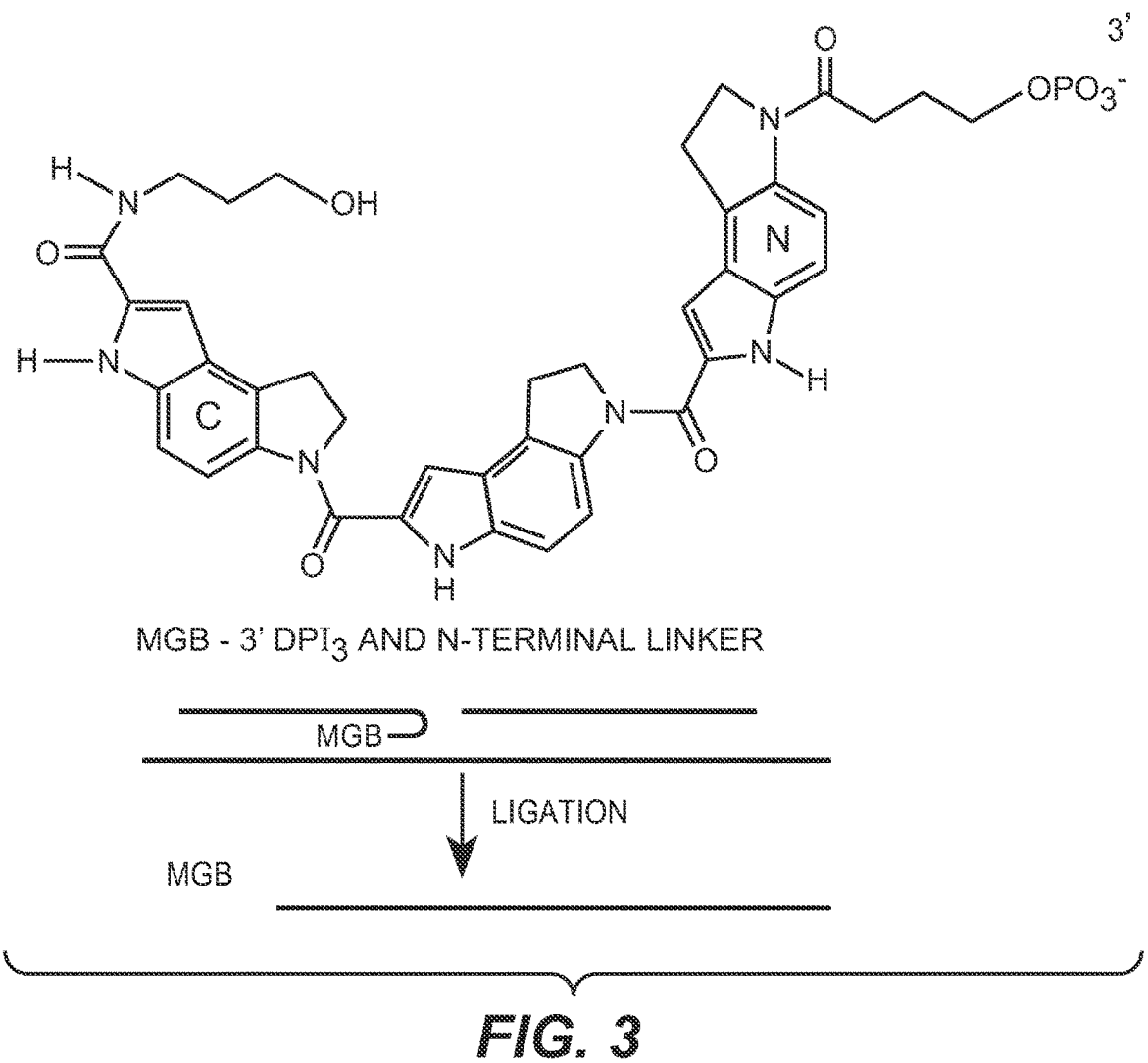
FIG. 3 depicts an embodiment utilizing a minor groove binder as a destabilization agent. Upon ligation, the MGB is removed, thus destabilizing the hybridization complex. (SEQ ID NOS: 1-2)

In one aspect of the invention, the upstream oligonucleotide is designed to have an additional nucleotide segment that does not bind to the target of interest, but is to be used to subsequently capture the ligated product on a solid support or device of some sort (FIG. 2A). In a preferred embodiment, the downstream oligonucleotide has a detectable label attach to it, such that following ligation, the resulting product will contain a capture sequence for a solid support at its 3' end and a detectable label at its 5' end, and only ligated products will contain both the capture sequence and the label (FIG. 2B).

For multiplex target detection, each upstream probe of a probe set is designed to have a unique sequence at is 3' end that corresponds to a different position on a DNA array. Each downstream probe of a probe set has a detectable label that is identical to the other down stream probes, but a unique target binding sequence that corresponds to its respective targets. Following hybridization of the oligonucleotide targets with the DNA array, only ligated probes that have both an address sequence (upstream probe) and a label (downstream probe) will be observable. In a more preferred embodiment, the probes have chemical ligation reaction moieties similar to those described by Abe (2004) such that multiple copies of ligated product are produced for each target.

In another aspect of the invention, the detectable label can be attached to upstream oligonucleotide and the capture sequence can be a part of the downstream oligonucleotide, such that the ligated products will have the detectable label more towards the 3' end and the capture sequence towards the 5' end of the ligated product. The exact configuration is best determined via consideration of the ease of synthesis as well as the characteristics of the devices to be used to subsequently detect the ligated reaction product.

The anchor sequence may have both nucleic and nonnucleic acid portions. Thus, for example, flexible linkers such as alkyl groups, including polyethylene glycol linkers, may be used to provide space between the nucleic acid portion of the anchor sequence and the support surface. This may be particularly useful when the ligation products are large.

In addition, in some cases, sets of anchor sequences that correspond to the capture probes of "universal arrays" can be used. As is known in the art, arrays can be made with synthetic "universal" sequences as capture probes, thus allowing these arrays to be used for any samples.

In one embodiment, one or more of the ligation probes comprise a label. By "label" or "labeled" herein is meant that a compound has at least one element, isotope or chemical compound attached to enable the detection of the compound, e.g. renders a ligation probe or ligation or transfer product detectable using known detection methods, e.g., electronic, spectroscopic, photochemical, or electrochemiluminescent methods. In general, labels fall into three classes: a) isotopic labels, which may be radioactive or heavy isotopes; b) magnetic, electrical, thermal; and c) colored or luminescent dyes; although labels include enzymes and particles such as magnetic particles as well. The dyes may be chromophores or phosphors but are preferably fluorescent dyes, which due to their strong signals provide a good signal-to-noise ratio. Suitable dyes for use in the invention include, but are not limited to, fluorescent lanthanide complexes, including those of Europium and Terbium, fluorescein, fluorescein isothiocyanate, carboxyfluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), and others described in the 6th Edition of the Molecular Probes Handbook by Richard P. Haugland, herein expressly incorporated by reference. Additional labels include nanocrystals or Q-dots as described in U.S. Ser. No. 09/315,584, herein expressly incorporated by reference.

In some embodiments, fluorescence resonance energy transfer (FRET) pairs are used in the compositions and methods of the reaction. As is described herein, transfer reactions may rely on the transfer of one of a FRET pair from one transfer probe to another, resulting in a differential signal, as is outlined below. In addition, ligation reactions may utilize FRET pairs, one on each probe, that upon ligation and removal from the target sequence allows detection based on a FRET signal. Other FRET systems are described herein. Suitable FRET pairs are well known in the art.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as is more fully described below. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95.degree. C.).

In a preferred embodiment, the binding partner pair comprises a primary detection label (for example, attached to a ligation probe) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$ to $10^{-6}$ $M^{-1}$, with less than about $10^{-5}$ to $10^{-9}$ $M^{-1}$ being preferred and $10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo-or hetero-bifunctional linkers as are well known (see 1994 Pierce Chemical Company catalog, technical section on cross-linkers, pages 155 200, incorporated herein by reference).

In this embodiment, the label may also be a label probe binding sequence or complement thereof. By "label probe" herein is meant a nucleic acid that is substantially complementary to the binding sequence and is labeled, generally directly. See for example FIG. 2A.

Methods of Making the Compositions

The compositions of the invention are generally made using known techniques. In general, methodologies based on standard phosphoramidite chemistries find particular use in the present invention, although as is appreciated by those in the art, a wide variety of nucleic acid synthesis reactions are known.

In the case of halo leaving group chemistries, the methods of making the probes is known in the art; see for example Abe et al., *Proc Natl Acad Sci USA* (2006)103(2):263-8; Silverman et al., *Nucleic Acids Res.* (2005) 33(15):4978-86; Cuppolletti et al., *Bioconjug Chem.* (2005) 16(3):528-34; Sando et al., *J Am Chem Soc.* (2004) 4; 126(4):1081-7; Sando et al., *Nucleic Acids Res* Suppl. (2002) 2:121-2; Sando et al., *J Am Chem Soc.* (2002) 124(10):2096-7; Xu et al., *Nat Biotechnol.* (2001) 19(2):148-52; Xu et al., *Nucleic Acids Res.* (1998) 26(13):3159-64; Moran et al., *Proc Natl Acad Sci U SA* (1997) 94(20):10506-11; Kool, U.S. Pat. No. 7,033,753; Kool, U.S. Pat. No. 6,670,193; Kool, U.S. Pat. No. 6,479,650; Kool, U.S. Pat. No. 6,218,108; Kool, U.S. Pat. No. 6,140,480; Kool, U.S. Pat. No. 6,077,668; Kool, U.S. Pat. No. 5,808,036; Kool, U.S. Pat. No. 5,714,320; Kool, U.S. Pat. No. 5,683,874; Kool, U.S. Pat. No. 5,674,683; and Kool, U.S. Pat. No. 5,514,546, each of which is incorporated herein by reference in its entirety.

Additional components such as labels, primer sequences, promoter sequences, etc. are generally incorporated as is known in the art. The spacing of the addition of fluorophores and quenchers is well known as well.

The invention provides a number of novel reagents associated with NPL for nucleic acid chemistry, including novel phosphoramidite chemistries to generate the thioester ligation reaction moieties. Ideally, thioester functionalities can be incorporated into oligonucleotides and oligonucleotide mimics as a routine part of solid phase synthesis, however it is also possible to incorporate thioester functionality by solution phase reaction of an oligonucleotide with a suitable reagent following cleavage from the solid support as discussed below.

Figure 10A:
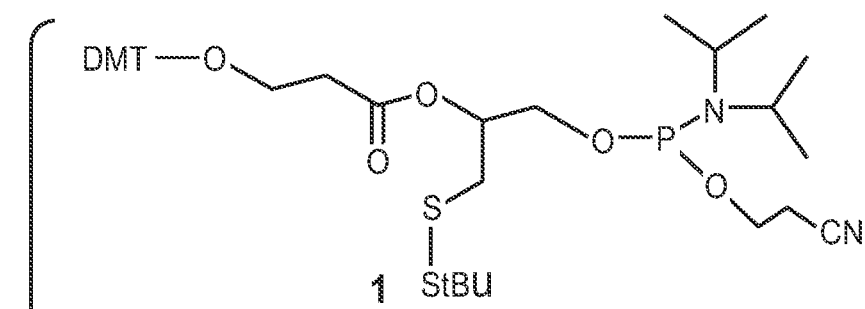
FIGS. 10A-C depict a number of compounds of use in the invention.
Figure 10A:
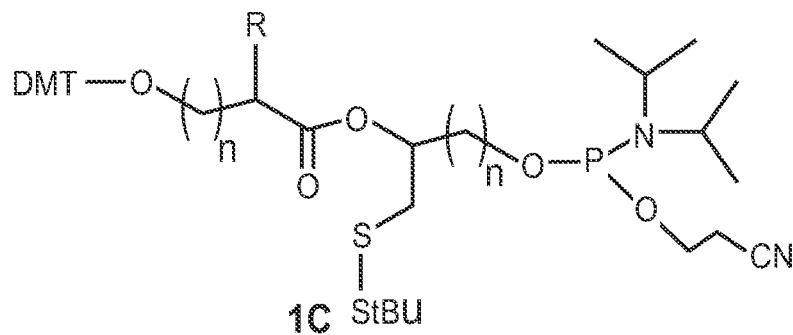
Figure 10A:
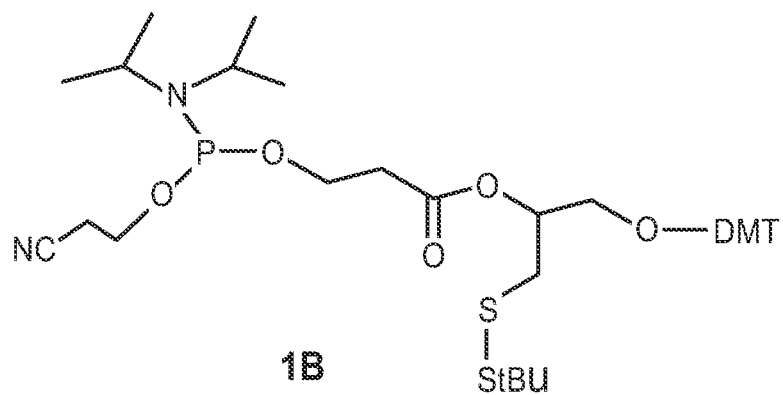
Figure 10A:
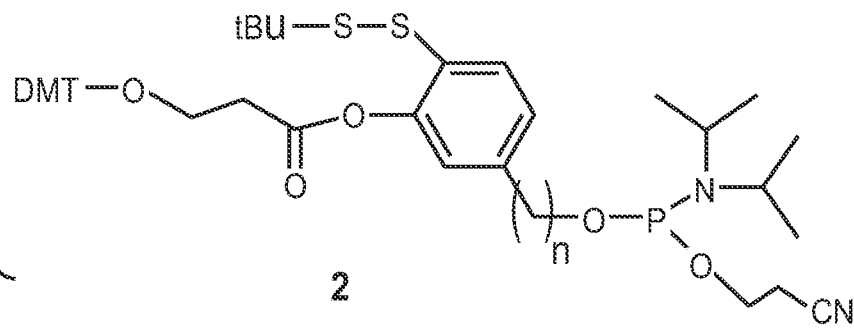
Figure 12:
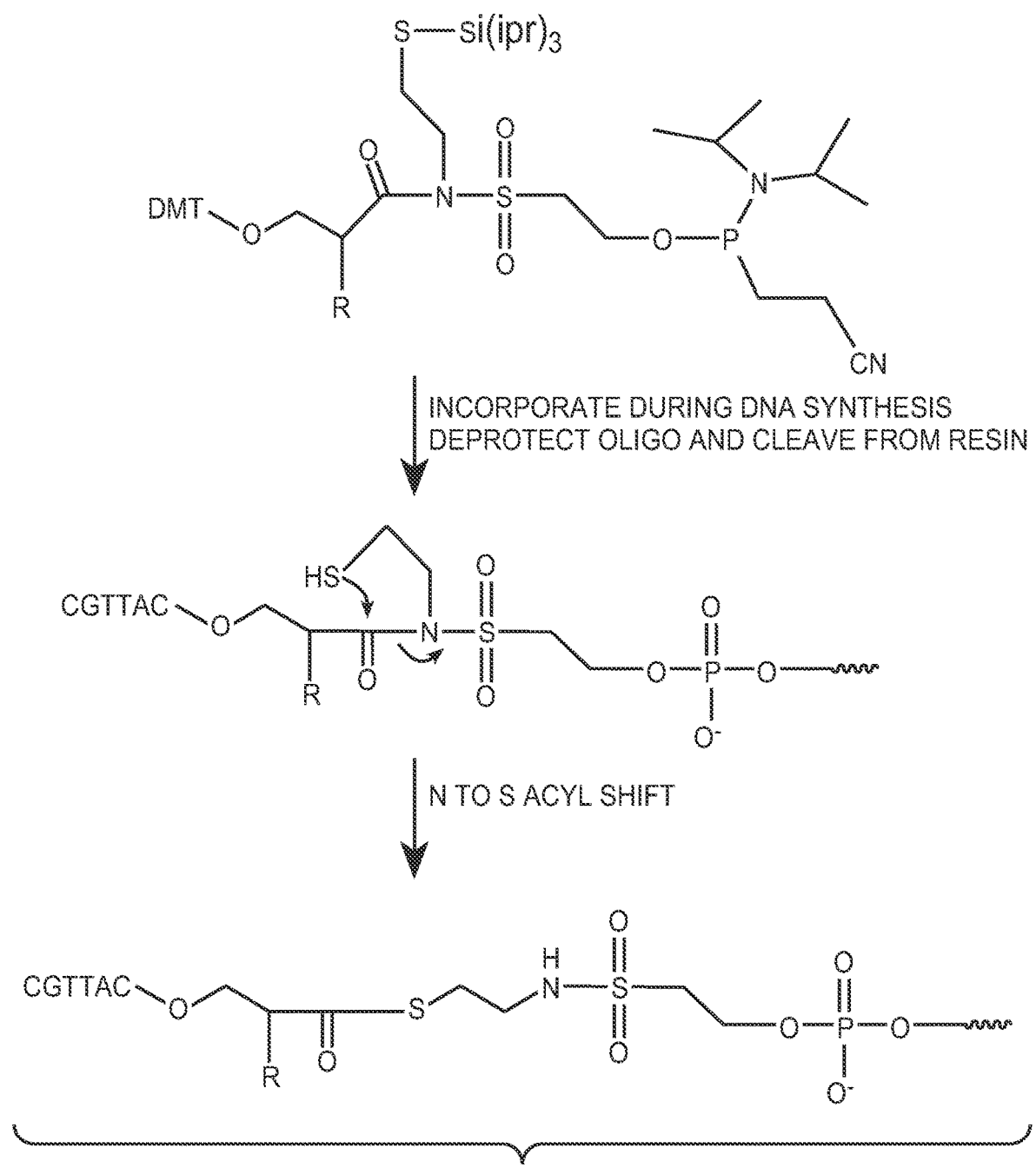
FIG. 12 depicts a schematic of an improved reaction for forming a thioester.
Figure 13:
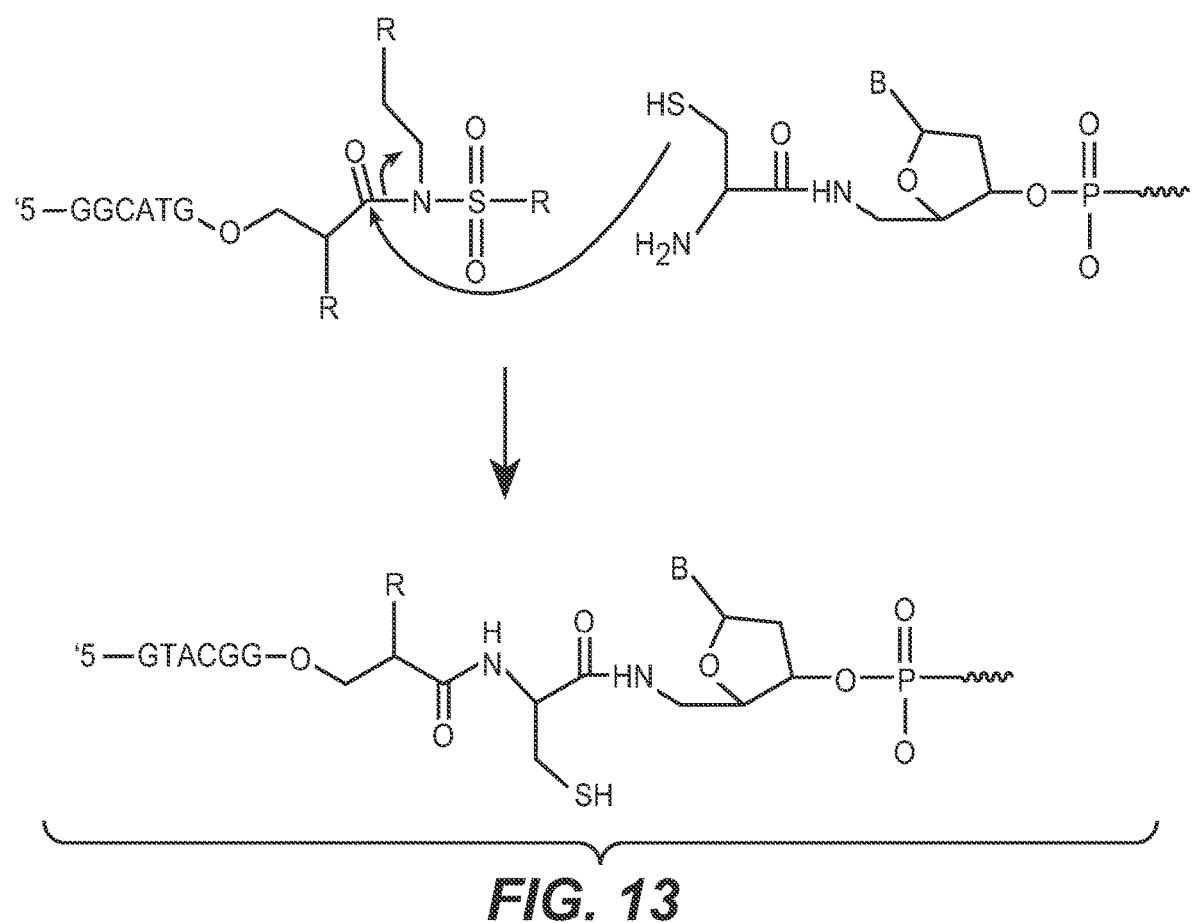
FIG. 13 shows a variation of the chemistry of FIG. 12.

As regards straight synthesis, it is possible to react a thiol containing oligonucleotide probe with an activated carboxyl group to produced thioester containing oligonucleotides. This will often be accomplished following complete deprotection of the oligonucleotide bases and will usually occur in the solution phase as oppose to while the probe is still attached to the solid support. However, due to the limited stability of the thioester moiety to nucleophilic attack and the nucleophilic/basic deprotection conditions that are a standard part of nucleic acid synthesis, direct incorporation of the thioester moiety during routine solid phase synthesis is problematic, although the present invention includes so doing. In an effort to overcome these limitations, "masked" thioester reagents that can be incorporated into nucleic acids as a part of routine DNA/RNA synthesis have been developed. During the initial synthesis, these reagents exist as non-thioester moieties, however following completion of the synthesis and base deprotection steps, these reagents are unmasked and able to rearrange to produce, at least transiently, the desired thioester. Some examples of "masked" thioester incorporating reagents are shown in the figures. All of the reagents are phosphoramidites with an internal ester functionality that is proximal to a protected thiol, in many cases the protected thiol is a disulfide as depicted in the figures, although other protecting groups are also suitable. The disulfide is a protected thiol moiety than can be easily removed under appropriate reaction conditions. Alternative sulfur protecting groups can also be utilized (Chan et al., Biochemistry. (2000) 39(24):7221-8). Molecules 1 and 2 of FIG. 10A are bifunctional reagents that can be used anywhere within the oligonucleotide sequence. Molecule 3 is a chain terminating reagent. A key feature of these molecules is the position of the thiol group relative to the ester group. This positioning allows for easy attack of the ester group by the thiol group to aid in the generation of the desired thioester moiety (FIG. 12). Previous work in peptide synthesis has demonstrated the utility of this approach (Botti et al., *Protein Pept. Lett*. (2005) 12(8):729-35 and Warren et al., *J Am. Chem. Soc*. (2004) 126(21):6576-82).

Figure 10B:
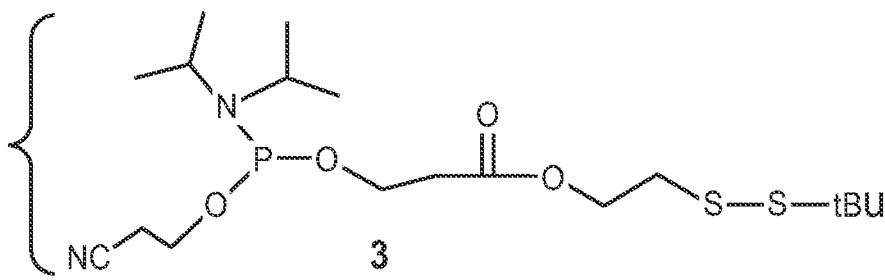
Figure 10C:
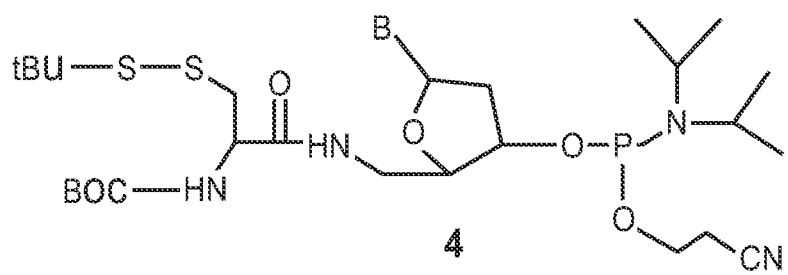
Figure 10C:
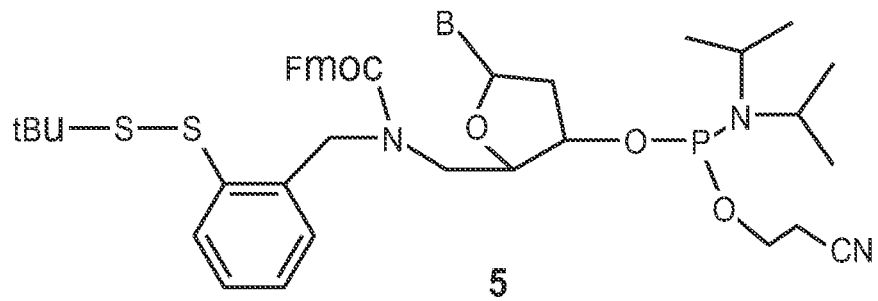
Figure 10C:
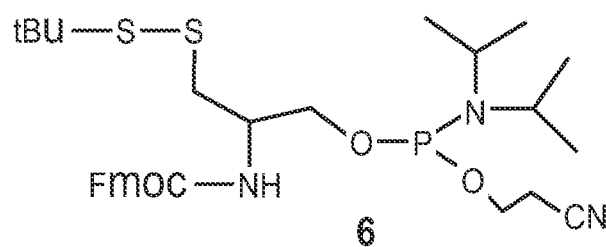
Figure 10C:
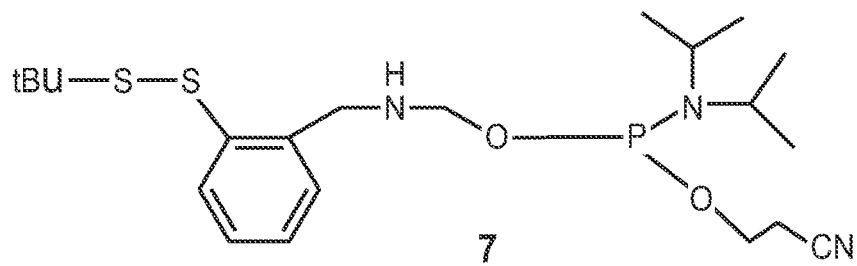
Figure 10C:
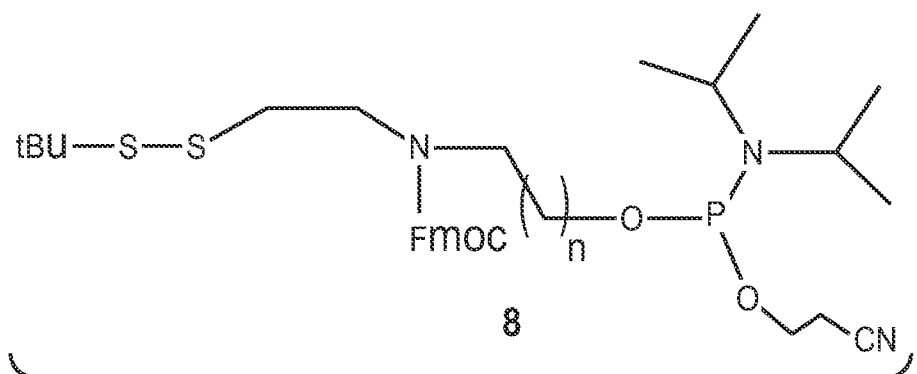
Figure 11A:
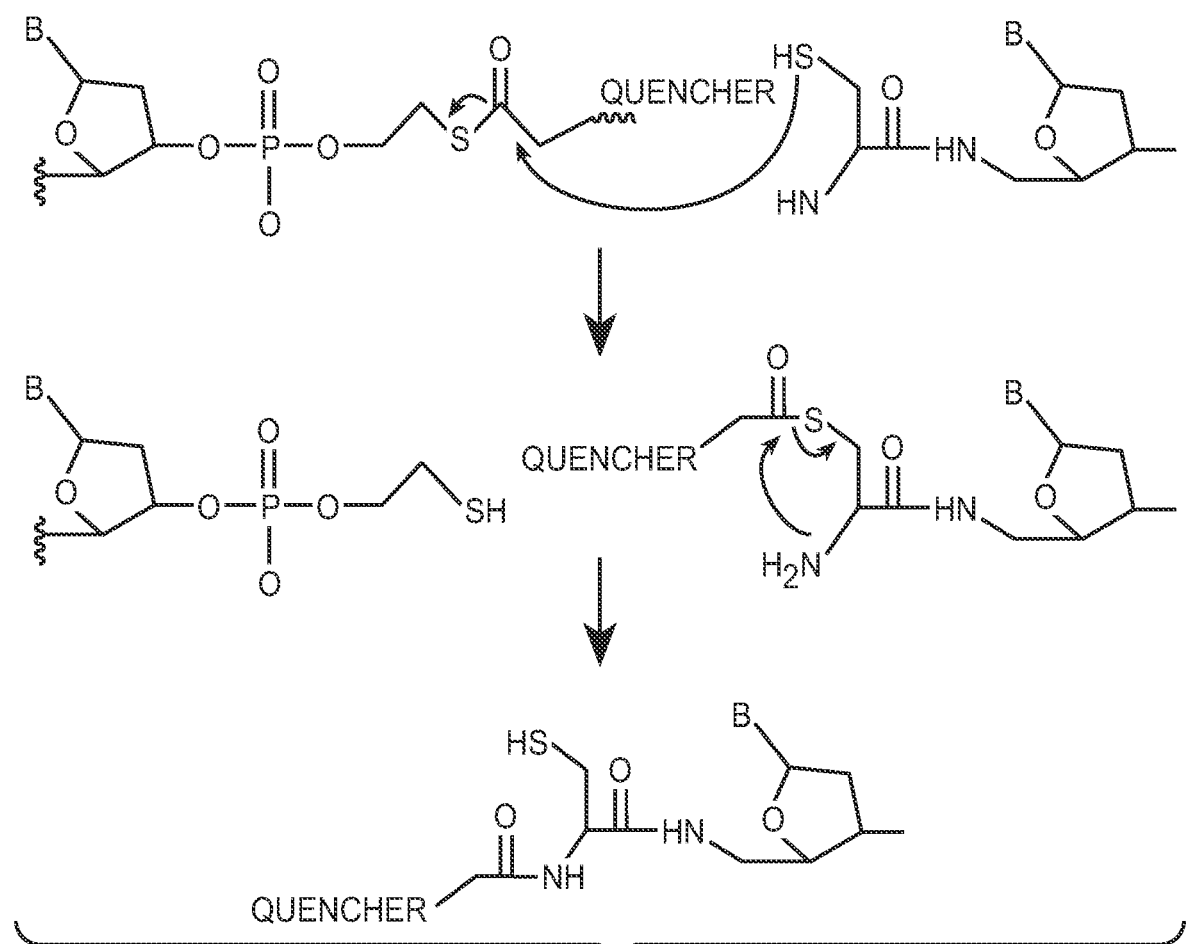
FIGS. 11A and 11B depicts a schematic using a reverse orientation of the thioester to result in a transfer reaction.
Figure 11B:
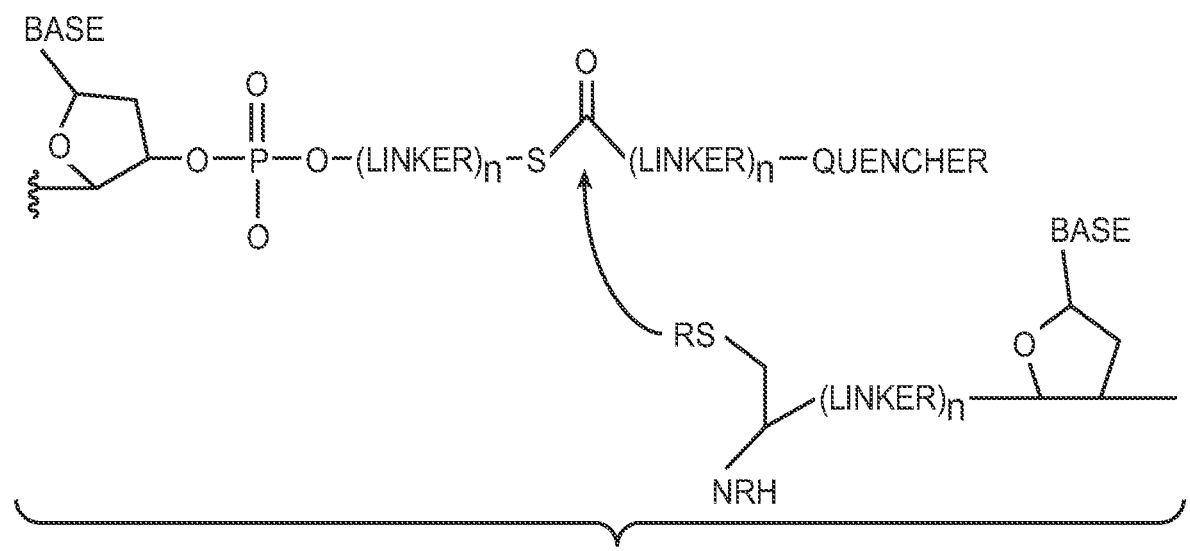

Reagents represented by Molecules 1-3 of FIG. 10A-B can be varied using techniques known in the art. For example, the length of the spacer between the thioester and either the phosphorous or O-DMT can be varied (see FIG. 10A, molecules 1B and 1C).

Another approach to incorporating a thioester group at the end of a synthetic oligonucleotide is to make use of a solid support with the specialty attached chemistry. One such attachment chemistry is a variation of the "safety-catch linker" that was originally described by Kenner in 1971 (*J. Chem. Soc*. (1971) pp. 636-637). This safety-catch linker makes use of an acylsulfonamide group that is initially very resistant to basic or strongly nucleophilic conditions, however following synthesis, the sulfonamide group can be activated by alkylation and it is then susceptible to nucleophilic attack. Furthermore, the reactivity of the alkylated sulfonamide group can be tuned by varying the electron withdrawing nature of the alkylating reagent as well as the nature of the linker chain (alkyl versus acyl). Exposure of the activated resin to thiol containing molecules can produced desired thioesters (Bakes, B. J. and Ellman, J. A., *J. Org. Chem.*, 64:2322-2330 (1990)). This safety-catch linker has recently been used by Ollivier (Ollivier 2006) for the synthesis of thioester terminated peptides.

Similar to the peptide case, the safety catch resin can be used to produce oligonucleotides with terminal thioester moieties. In this case, an oligonucleotide is synthesized on a solid support with the desired acylsulfonamide group functionality. Following completion of the synthesis and deprotection of the bases, the support is alkylated and the oligonucleotide is released following treatment with a thiol containing compound like mercaptoethanol or benzyl mercaptan. Potential drawbacks of this approach are the potential for alkylation of the DNA bases and being limited to producing oligonucleotides with terminal thioester functionality.

An alternative approach is to synthesize phosphoramidite reagents that possess an internal acylsulfonamide group 9. Following alklyation and treatment with a suitable thiol containing compound, this reagent can be converted into a thioester. Alternatively, a reagent like 10 can be synthesized. The acylsulfonamide is prealkylated with a protected thiol which following removal of the protecting group will rearrange to produce an internal thioester without cleavage from the resin. Furthermore, the stability and reactivity of the 9 and 10 can be tuned by changing the electron-withdrawing nature of R. It should also be noted that the R group depicted in Compounds 9 and 10 may be absent, as may be the carbon to which it is attached.

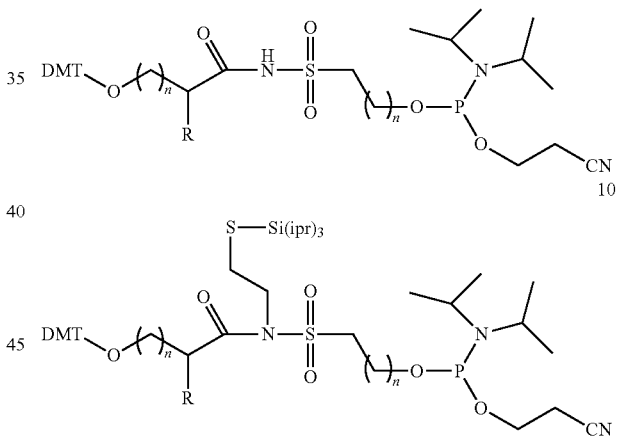

In addition to producing probes with thioester functionality, it is also desirable to produce probes with nucleophilic groups at the terminus (e.g. the nucleophile ligation moieties). In the case of probe sets that will make use of the NPL chemistry, it is desirable to produce probes with a free thiol group that is proximal to a primary or secondary amine. IN general, primary amine containing probes will ligate and rearrange faster than secondary amine containing probes. The phosphoramidite described by Stetsenko and Gait (*J Org Chem*. (2000) 65(16):4900-8) can be used to produce oligonucleotides with the common 1-amino, 2-thiol reactive groups, however this amidite does not necessarily give the desired bond lengths for preferred alignment and reactivity during the ligation reaction. Reagents like 4 and 6 can be used to produce probes with the cysteine like 1-amino, 2-thiol functionality that is most often used for native peptide ligation.

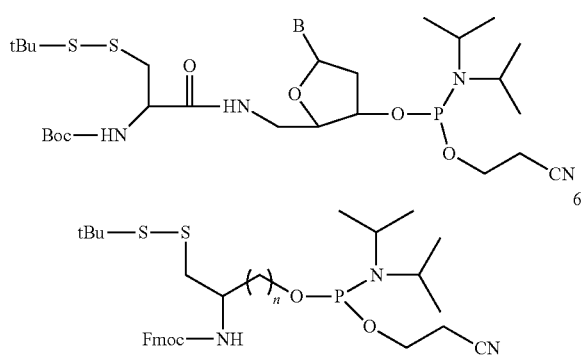

4

6

In general, methods of making the downstream ligation moiety of NPL, e.g. the nucleophile ligation moiety, is well known in the art.

Alternatively, reagents 5, 7, and 11 will undergo a similar reaction, however they will rearrange to decrease the distance between the ligated probes. This rearrangement can lead to a destabilization of the ligated probe and increased product turnover.

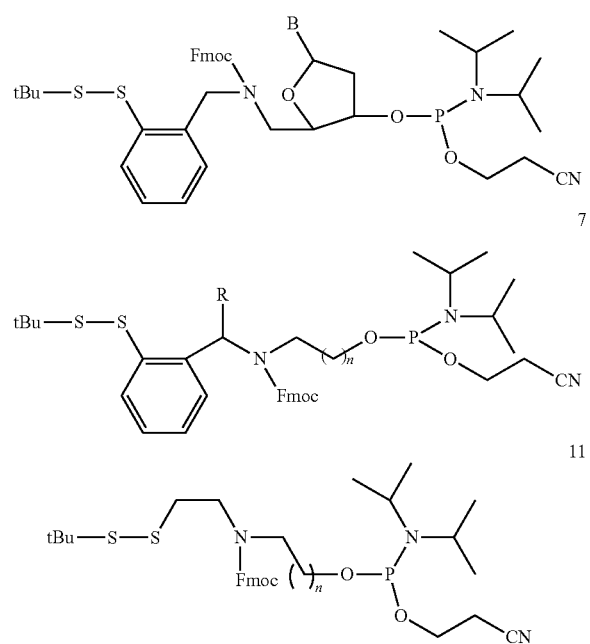

5

7

11

Secondary Reactions

In addition, prior to detecting the ligation or transfer reactions, there may be additional amplification reactions. That is, it is possible to design secondary amplification reactions that can be used to increase the signal for detection of the target sequence; e.g. by increasing the number of ligated products produced per copy of target. In one embodiment, any number of standard amplification reactions can be done to the ligation product, including, but not limited to, strand displacement amplification (SDA), nucleic acid sequence based amplification (NASBA), ligation amplification and the polymerase chain reaction (PCR; including a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", among others. In one embodiment, the amplification technique is not PCR. According to certain embodiments, one may use ligation techniques such as gap-filling ligation, including, without limitation, gap-filling OLA and LCR, bridging oligonucleotide ligation, FEN-LCR, and correction ligation. Descriptions of these techniques can be found, among other places, in U.S. Pat. No. 5,185,243, published European Patent Applications EP 320308 and EP 439182, published PCT Patent Application WO 90/01069, published PCT Patent Application WO 02/02823, and U.S. patent application Ser. No. 09/898,323.

Figure 9:
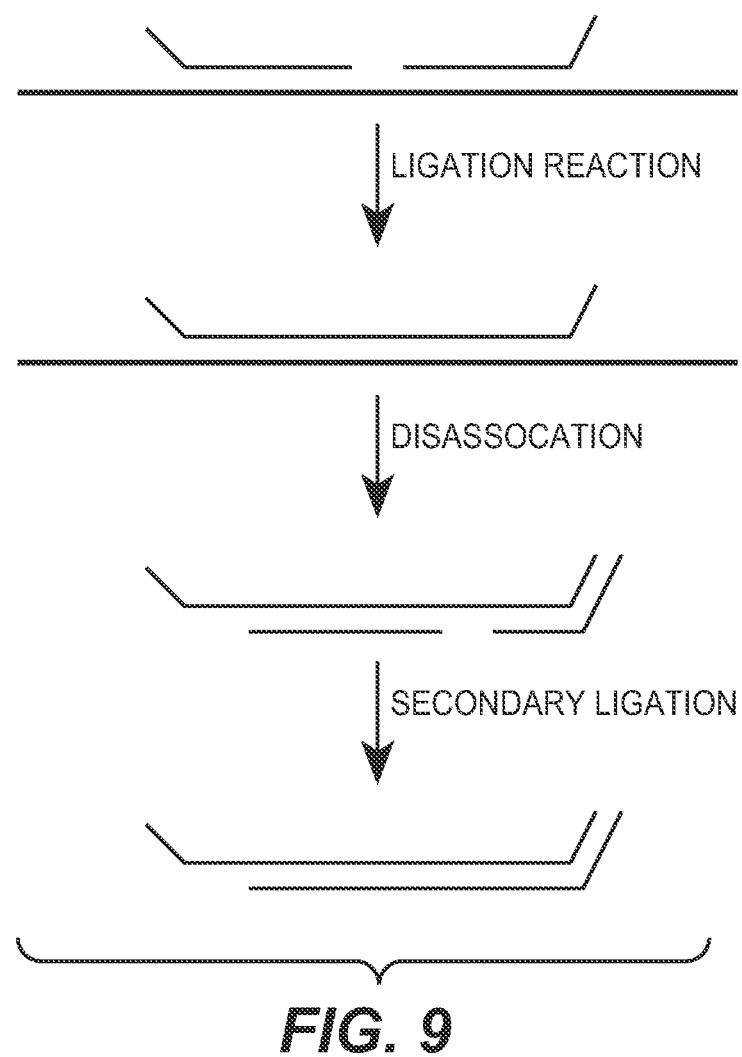
FIG. 9 depicts a schematic of a "nested" or secondary ligation reaction for either specificity or amplification.

In addition to standard enzymatic amplification reactions, it is possible to design probe schemes where the ligated product that is initially produced can itself be the target of a secondary chemical ligation reaction (FIG. 9).

Furthermore, "preamplification reactions" can be done on starting sample nucleic acids to generate more target sequences for the chemical reaction ligation. For example, whole genome amplification can be done.

Assays

As will be appreciated by those in the art, the assays utilizing methods and compositions of the invention can take on a wide variety of configurations, depending on the desired application, and can include in situ assays (similar to FISH), solution based (e.g. homogeneous) assays (e.g. transfer/removal of fluorophores and/or quenchers), and heterogeneous assays (e.g. utilizing solid supports for manipulation, removal and/or detection, such as the use of high density arrays). In addition, the assays can include additional reactions, such as pre-amplification of target sequences and secondary amplification reactions after ligation has occurred, as is outlined herein.

As shown herein, ligation reactions as well as transfer reactions can be done. Transfer reactions involve methods and compositions which change the nature of the product that is formed during the chemical ligation reaction. Most of the work to date has focused on the ligation of two or more oligonucleotides to form a longer oligonucleotide fragment post reaction. However, it is often desirable not to make a longer oligonucleotide probe post reaction, but to produce products that can be distinguished from the unreacted starting materials. Thus, instead of producing longer oligonucleotides, the invention provides methods for attaching a detectable label during the ligation reaction (FIG. 14). For example, one approach is to transfer/label one of the oligonucleotides with a fluorescent quencher like Dabcyl during the course of the ligation reaction. This approach has been described by Grossman (Grossman 2007) in which a Dabcyl quencher was transferred from one oligonucleotide probe to another while bound to a DNA target. In addition to a fluorescent quencher like Dabcyl, it is also possible to use any number of other labels, as outlined herein. There are a wide variety of molecules and materials that a probe can be labeled with, and ideally, these labels should result in a minimal increase in "labeled" probe binding strength post reaction. In a preferred embodiment, these labels also serve to decrease the Tm of the probe. In some embodiments, systems based on FRET can be manipulated such that signals increase or decrease based on orientation.

The assays described herein generally rely on increases in signal, e.g. the generation of fluorescence or chemiluminescence, etc., rather than decreases. However, as will be appreciated by those in the art, assays that rely on decreases in signal are also possible.

In one embodiment, the reactions are done "in situ" (also referred to in various assay formats as "in vitro" and/or "ex vivo" depending on the sample), similar to FISH reactions. Since no exogenous enzymes need to be added, reagents can be added to cells (living, electroporated, fixed, etc.) such as histological samples for the determination of the presence of target sequences, particularly those associated with disease states or other pathologies. In this embodiment, preferred systems include the use of reactions that generate a signal, particularly a fluorescent signal. For example, in this embodiment, preferred embodiments utilize leaving groups that comprise quencher moieties, such that upon a transfer or ligation reaction, an increase in fluorescence is produced. Similarly, these embodiments can utilize ligation of probes each comprising a FRET pair such that upon ligation FRET occurs.

In addition, "in vitro" assays can be done where target sequences are extracted from samples. Samples can be processed (e.g. for paraffin embedded samples, the sample can be prepared), the reagents added and the reaction allowed to proceed, with detection following as is done in the art.

In many embodiments, the ligated products are detected using solid supports. In one embodiment, the ligated products are attached to beads, using either anchor probe/capture probe hybridization or other binding techniques, such as the use of a binding partner pair (e.g. biotin and streptavidin). For example, in one embodiment, a transfer reaction results in a biotin moiety being transferred from the first ligation probe to a second ligation probe comprising a label. Beads comprising streptavidin are contacted with the sample, and the beads are examined for the presence of the label, for example using FACS technologies.

In some embodiments, the ligated products are detected using heterogeneous assays. That is, the reaction is done is solution and the product is added to a solid support, such as an array or beads. Generally, one ligation probe comprises an anchor sequence or a binding pair partner (e.g. biotin, haptens, etc.) and the other comprises a label (e.g. a fluorophore, a label probe binding sequence, etc.). The ligated product is added to the solid support, and the support optionally washed. IN this embodiment, only the ligated product will be captured and be labeled.

In another aspect of the invention, one of oligonucleotide probes has an attached magnetic bead or some other label (biotin) that allows for the easy manipulation of the ligated product. The magnetic bead or label can be attached to either the upstream oligonucleotide or the downstream oligonucleotide using any number of configurations as outlined and suggested herein.

As described herein, secondary reactions can also be done, where additional functional moieties (e.g. anchor sequences, primers, labels, etc.) are added. Similarly, secondary amplification reactions can be done as described herein.

Detection systems are known in the art, and include optical assays (including fluorescence and chemiluminescent assays), enzymatic assays, radiolabelling, surface plasmon resonance, magnetoresistance, cantilever deflection, surface plasmon resonance, etc. In some embodiments, the ligated product can be used in additional assay technologies, for example, as described in 2006/0068378, hereby incorporated by reference, the ligated product can serve as a linker between light scattering particles such as colloids, resulting in a color change in the presence of the ligated product.

In some embodiments, the detection system can be included within the sample collection tube; for example, blood collection devices can have assays incorporated into the tubes or device to allow detection of pathogens or diseases.

Solid Supports

As outlined above, the assays can be run in a variety of ways. In assays that utilize detection on solid supports, there are a variety of solid supports, including arrays, that find use in the invention.

IN some embodiments, solid supports such as beads find use in the present invention. For example, binding partner pairs (one on the ligated product and one on the bead) can be used as outlined above to remove non-ligated reactants. In this embodiment, magnetic beads find particular use.

In some embodiments, the capture probes of the invention are attached to solid supports for detection. For example, capture probes can be attached to beads for subsequent analysis using FACS. Similarly, bead arrays as described below may be used.

In one embodiment, the present invention provides arrays, each array location comprising at a minimum a covalently attached nucleic acid probe, generally referred to as a "capture probe". By "array" herein is meant a plurality of nucleic acid probes in an array format; the size of the array will depend on the composition and end use of the array. Arrays containing from about 2 different capture ligands to many thousands can be made. Generally, the array will comprise from two to as many as 100,000 or more, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture probe may be made as well. In addition, in some arrays, multiple substrates may be used, either of different or identical compositions. Thus, for example, large arrays may comprise a plurality of smaller substrates. Nucleic acids arrays are known in the art, and can be classified in a number of ways; both ordered arrays (e.g. the ability to resolve chemistries at discrete sites), and random arrays (e.g. bead arrays) are included. Ordered arrays include, but are not limited to, those made using photolithography techniques (Affymetrix GeneChip™), spotting techniques (Synteni and others), printing techniques (Hewlett Packard and Rosetta), electrode arrays, three dimensional "gel pad" arrays, etc. Liquid arrays may also be used.

In a preferred embodiment, the arrays are present on a substrate. By "substrate" or "solid support" or other grammatical equivalents herein is meant any material that can be modified to contain discrete individual sites appropriate for the attachment or association of nucleic acids. The substrate can comprise a wide variety of materials, as will be appreciated by those in the art, including, but not limited to glass, plastics, polymers, metals, metalloids, ceramics, organics, etc.n When the solid support is a bead, a wide variety of substrates are possible, including magnetic materials, glass, silicon, dextrans, plastics, etc.

Hardware

Microfluidics

In another aspect of the invention, a fluidic device similar to those described by Liu (2006) is used to automate the methodology described in this invention. See for example U.S. Pat. No. 6,942,771, herein incorporated by reference for components including but not limited to cartridges, devices, pumps, wells, reaction chambers, and detection chambers.

In a preferred embodiment, the devices of the invention comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtitler plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of heat exchangers such as controlled blocks or platforms to provide accurate temperature control of incubating samples from 0.degree. C. to 10.degree. C.; this is in addition to or in place of the station thermocontrollers.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In a preferred embodiment, useful detectors include a microscope(s) with multiple channels of fluorescence; plate readers to provide fluorescent, electrochemical and/or electrical impedance analyzers, ultraviolet and visible spectrophotometric detection with single and dual wavelength endpoint and kinetics capability, fluroescence resonance energy transfer (FRET), luminescence, quenching, two-photon excitation, and intensity redistribution; CCD cameras to capture and transform data and images into quantifiable formats; and a computer workstation.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

Kits

In another aspect of the invention, a kit for the routine detection of a predetermined set of nucleic acid targets is produced that utilizes a chemical ligation reaction as part of the detection process.

EXAMPLES

T*=Fluorescein dT (Glen Research)
D1=5'-L-ACT*CCGACCTTCACCA-3' (SEQ ID NO: 3)
D2=5'-L-ACT*GTGGTCATGAG-3' (SEQ ID NO: 4)
Thio 1=5-ACCAAATCCGTT-S-3' (SEQ ID NO: 5)
Thio 2=5'-AGTGATGGCATG-S-3' (SEQ ID NO: 6)

Figure 15:
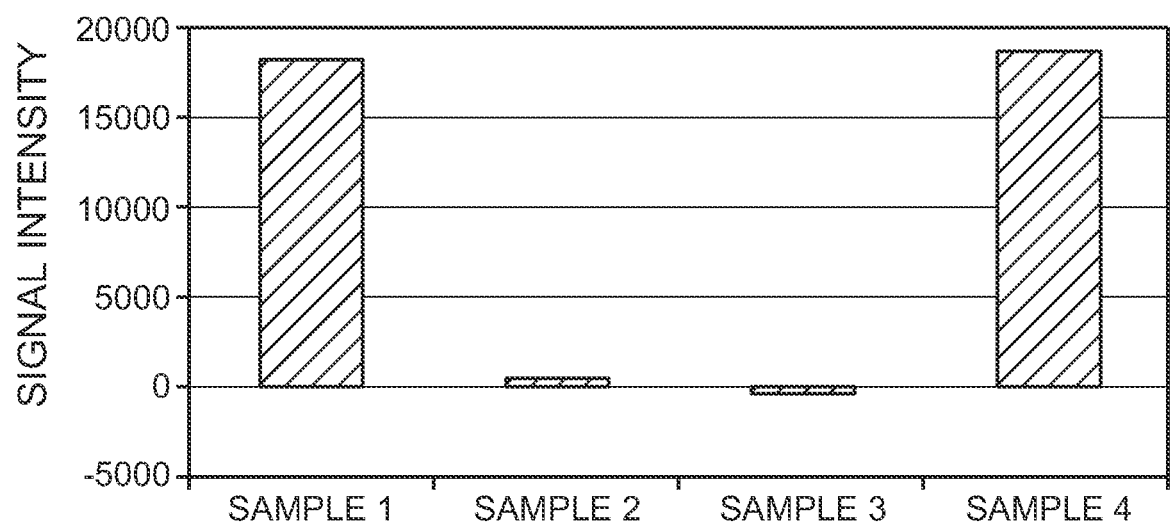
FIG. 15 show the results of Example 1.

Target 1=5'-TGAAGGTCGGAGTAACGGATTTG-GTCGTA-3' (SEQ ID NO: 7)
Target 2=5'-CATGACCACAGTCATGCCATCACTGCCA-3' (SEQ ID NO:8)
In a 200 ul PCR tube suitable for real time fluorescence monitoring was added 100 nM target (Target 1 or Target 2), 500 nM 3' phosphothioate labeled probe (Thio 1 or Thio 2) and 500 nM Dabsyl and Fluorescein labeled probe (D1 or D2) in 50 ul of buffer solution (60 mM Pipes Buffer, pH 7.0, 10 mM MgCl2, 50 uM DTT, and 1 ug/ml Salmon Sperm DNA). The solutions were mixed and loaded into a Stratagene Mx3000P real-time PCR instrument. The samples were incubated at 30° C. and the fluorescence was measured in the FAM channel of the instrument every 5 minutes over a 1 hour period. Reactions were performed in duplicate and the data was averaged. Data was baseline corrected using no target control samples. The signals observed for the various samples at the 1 hour time point are shown FIG. 15.

Sample 1=Target 1, Thio 1 and D1
Sample 2=Target 2, Thio 1 and D1
Sample 3=Target 1, Thio 2 and D2
Sample 4=Target 2, Thio 2 and D2

What is claimed is:

1. A method for detecting the presence of a known target nucleic acid in a sample comprising:
   a) providing a ligation substrate comprising:
      i) said known target nucleic acid comprising a first target domain and an adjacent second target domain, wherein the first target domain is upstream of the second target domain;
      ii) a first nucleic acid ligation probe comprising:
         1) a first probe domain hybridized to said first target domain; and
         2) a 5'-ligation moiety; and
      iii) a second nucleic acid ligation probe comprising:
         1) a second probe domain hybridized to said second target domain;
         2) a 3' ligation moiety;
      wherein at least one of said first and said second ligation probes comprises an anchor sequence;
   b) ligating said first and said second ligation probes in the absence of a ligase enzyme to form a ligation product;
   c) capturing said ligation product on a substrate comprising a capture probe that hybridizes to said anchor sequence; and
   d) detecting the presence of said ligation product thereby detecting the presence of said target nucleic acid.

2. A method according to claim 1 wherein said first and second ligation moieties form a ligation moiety pair selected from the group consisting of a) a thioester and a nucleophile and b) a dimethylamino(azobenzene) sulfonyl (DABSYL) moiety and a phosphothioate moiety.

3. A method according to claim 1 wherein said sample is selected from the group consisting of a mammalian bodily fluid and a mammalian paraffin embedded tissue sample.

4. A method according to claim 1 wherein the other of said first and second ligation probes comprises a detectable label.

5. A method according to claim 4 wherein said detectable label is a fluorophore.

6. A method according to claim 1 wherein the other of said first and second ligation probes comprises a label binding sequence, and said ligated product further comprises a label probe hybridized to said binding sequence, wherein said label probe comprises a detectable label.

7. A method according to claim 1 wherein said target nucleic acid is DNA.

8. A method according to claim 1 wherein said known target nucleic acid is RNA.

9. A method for detecting the presence of a known target nucleic acid in a sample comprising:
   a) providing a ligation substrate comprising:
      i) said known target nucleic acid comprising a first target domain and an adjacent second target domain, wherein the first target domain is upstream of the second target domain;
      ii) a first nucleic acid ligation probe comprising:
         1) a first probe domain hybridized to said first target domain; and
         2) a 5'-ligation moiety; and iii) a second nucleic acid ligation probe comprising:
   1) a second probe domain hybridized to said second target domain;
   2) a 3' ligation moiety;
wherein said first and second ligation moieties form a ligation moiety pair selected from the group consisting of a) a thioester and a nucleophile and b) a dimethyl-amini(azobenzene) sulfonyl (DABSYL) moiety and a phosphothioate moiety, and wherein at least one of said first and said second nucleic acid ligation probes comprises an anchor sequence;
b) ligating said first and said second ligation probes in the absence of a ligase enzyme to form a ligation product;
c) capturing said ligation product on a substrate comprising a capture probe complementary to said anchor sequence; and
d) detecting the presence of said ligation product.

10. A method for detecting the presence of a known target nucleic acid in a sample, wherein said sample is selected from the group consisting of a mammalian bodily fluid and a mammalian paraffin embedded tissue sample, said method comprising:

a) providing a ligation substrate comprising:
   i) said known target nucleic acid comprising a first target domain and an adjacent second target domain, wherein the first target domain is upstream of the second target domain;
   ii) a first nucleic acid ligation probe comprising:
      1) a first probe domain hybridized to said first target domain; and
      2) a 5'-ligation moiety; and
   iii) a second nucleic acid ligation probe comprising:
      1) a second probe domain hybridized to said second target domain;
      2) a 3' ligation moiety;
wherein at least one of said first and said second nucleic acid ligation probes comprises an anchor sequence;
b) ligating said first and said second ligation probes in the absence of a ligase enzyme to form a ligation product;
c) capturing said ligation product on a substrate comprising a capture probe complementary to said anchor sequence; and
d) detecting the presence of said ligation product.

\* \* \* \* \*